United States Patent
Teply et al.

(10) Patent No.: US 9,340,543 B2
(45) Date of Patent: May 17, 2016

(54) HELQUAT DERIVATIVES, PREPARATION THEREOF, AND USE THEREOF AS MEDICAMENTS

(71) Applicant: USTAV ORGANICKE CHEMIE A BIOCHEMIE AKADEMIE VED CR, V.V.I., Prague (CZ)

(72) Inventors: Filip Teply, Roztoky u Prahy (CZ); Miroslav Hajek, Prague (CZ)

(73) Assignee: USTAV ORGANICKE CHEMIE A BIOCHEMIE AKADEMIE VED CR, V.V.I., Prague (CZ)

( * ) Notice: Subject to any disclaimer, the term of this patent is extended or adjusted under 35 U.S.C. 154(b) by 0 days.

(21) Appl. No.: 14/655,999

(22) PCT Filed: Jan. 17, 2014

(86) PCT No.: PCT/CZ2014/000009
§ 371 (c)(1),
(2) Date: Jun. 26, 2015

(87) PCT Pub. No.: WO2014/111069
PCT Pub. Date: Jul. 24, 2014

(65) Prior Publication Data
US 2015/0344477 A1    Dec. 3, 2015

(30) Foreign Application Priority Data

Jan. 17, 2013 (CZ) ...................... 2013-32

(51) Int. Cl.
| | | |
|---|---|---|
| C07D 471/22 | (2006.01) | |
| C07D 401/10 | (2006.01) | |
| C07D 455/03 | (2006.01) | |
| A61K 31/44 | (2006.01) | |
| A61P 35/00 | (2006.01) | |

(52) U.S. Cl.
CPC ............ C07D 471/22 (2013.01); C07D 401/10 (2013.01); C07D 455/03 (2013.01)

(58) Field of Classification Search
CPC ... C07D 471/22; C07D 401/10; C07D 455/03
USPC ........................................................ 546/38
See application file for complete search history.

(56) References Cited

FOREIGN PATENT DOCUMENTS

| | | |
|---|---|---|
| WO | 03/097642 A1 | 11/2003 |
| WO | 2009/047791 A2 | 4/2009 |
| WO | 2010/118711 A2 | 10/2010 |

OTHER PUBLICATIONS

Adriaenssens; Chem. Eur. J. 2009, 15, 1072-1076.*
Arai; Bulletin of the Chemical Society of Japan 1991, 64, 1996-1998.*

International Search Report for PCT/CZ2014/000009 filed Jan. 17, 2014.
International Patentabiltiy Report and Written Opinion for PCT/CZ2014/000009 filed Jan. 17, 2014.
Dora Balogh et al: "Helquat-Induced Chiroselective Aggregation of Au NPs", Nano Letters, vol. 12, No. 11, Nov. 14, 2012, p. 5835-5839.

* cited by examiner

*Primary Examiner* — Janet L Andres
*Assistant Examiner* — Daniel Carcanague
(74) *Attorney, Agent, or Firm* — Notaro, Michalos & Zaccaria P.C.

(57) ABSTRACT

The invention provides helquat derivatives of general formula I, wherein substituents $R^1$ and $R^2$ are independently selected from a group comprising H and $C_1$ to $C_3$ alkyl; up to three of $S^{1,2}$, $S^{1',2'}$, $S^{3,4}$ and $S^{3',4'}$ are present, each of $S^{1,2}$, $S^{1',2'}$, $S^{3,4}$ and $S^{3',4'}$ independently represents a linker consisting of a bivalent hydrocarbon chain having 3-6 carbon atoms; one or two atoms selected from the carbon atoms with the descriptor 2, 4, 2', and 4' are substituted with a substituent $R^3$ of general formula II or general formula III wherein $R^4$ is substituted or unsubstituted aryl; $T^1$ and $T^2$ independently represent a bivalent hydrocarbon chain having 2-5 carbon atoms; and anions $(X^1)^-$ and $(X^2)^-$ independently represent anions of pharmaceutically acceptable salts.

The helquat derivatives are useful as medicaments in the treatment of diseases related to increased cellular proliferation, such as oncologic diseases.

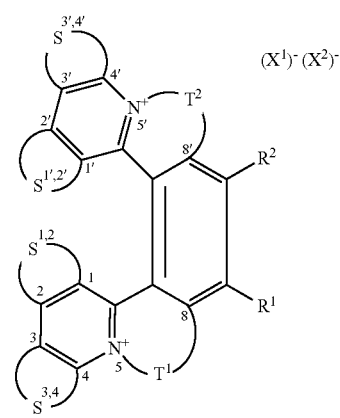

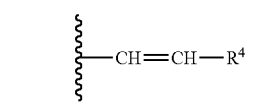

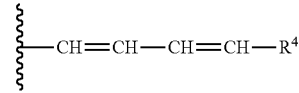

10 Claims, No Drawings

HELQUAT DERIVATIVES, PREPARATION THEREOF, AND USE THEREOF AS MEDICAMENTS

TECHNICAL FIELD

The invention relates to new helquat derivatives, preparation thereof, and use thereof as medicaments for treatment of diseases related to increased cellular proliferation.

BACKGROUND ART

Original compounds useful in cancer therapy are subject of interest in industrial and academic laboratories [Avendano, C., Menendez, J. C. (2008) Medicinal Chemistry of Anticancer Drugs, Elsevier Science, 1st edition].

Malignant tumor diseases are the most frequent cause of death [Siegel R. et al. (2012), *CA Cancer J. Clin.* 62, 10-29]. The uncontrolled cellular growth is linked to inherited genetic factors as well as environmental factors. For initiation and development of a malignant disease, the accumulation of several various genetic or epigenetic changes is necessary. This leads to transformation of a healthy cell into a fully malignant phenotype [Stratton M. R. (2011), *Science* 331, 1553-1558]. Cumulation of gene mutations leads to perturbations in normal functioning of proteins encoded by these genes. The proteins take part mainly in the regulation of cell division and differentiation, in the control of DNA replication fidelity, in the regulation of apoptosis of the damaged cells, in intercellular communication and intracellular signaling pathways [Hanahan D., Weinberg R. A. (2000), *Cell* 100, 57-70]. Malignant cells, unlike benign cells, have the ability to penetrate into the surrounding healthy tissue (invasiveness). Cancer cells are can be released from the original tumor and spread through the bloodstream or lymphatic system to distant parts of the body to form new tumors (metastatic process) [Nguyen D. X. et al. (2009), *Nat. Rev. Cancer* 9, 274-284].

The aim of anticancer therapy is to selectively induce apoptosis in the undesirable cancer cells, while not affecting the surrounding healthy tissue. Cytotoxic therapeutics act through DNA damage or microtubule damage and their specificity towards tumor cells in human body is due to their ability to selectively kill fast-proliferating cells. This selectivity can be determined by their cytostatic effects in cell culture in vitro [Chabner B. A., Roberts T. G (2005), *Nat. Rev. Cancer* 5, 65-72; Lüllmann H. et al. (2005), Farmakologie a toxikologie, Grada, 15th edition].

The fact that tumor cells are derived from cells of a host organism is a limiting factor for achieving the maximal selectivity of the cytotoxic effect. The sensitivity of cancer cells towards treatment is determined by the growth fraction of a tumor (the ratio of proliferating and non-proliferating tumor cells), the site of action of the cytostatic agent within the cell cycle, and the natural and the acquired resistance of the tumor cells against the cytostatics.

The present invention opens a straightforward way for obtaining novel compounds, structurally belonging to the helquat family and useful as therapeutics for diseases related to increased cellular proliferation.

Recently, papers describing synthesis of helical extended diquats (helquats) have been published [Adriaenssens et al. (2009), *Chem. Eur. J.* 15, 1072-1076; Severa et al. (2010), *Tetrahedron* 66, 3537-3552; Vavra et al. (2012), *Eur. J. Org. Chem.* 489-499]. They represent a new and therefore unexplored class of compounds with dicationic helical skeleton. The basic helquat skeletons described heretofore are composed so that each skeleton contains two quaternary N-heteroaromatic units which introduce two positively charged centers into the system, e.g. in the form of pyridinium, quinolinium, or isoquinolinium cationic moieties. Hence, a typical helquat arrangement is associated with dicationicity and with helical chirality at the same time. This combination has not been studied before in the context of small aromatic organic molecules.

A disadvantage of the heretofore described synthesis of these compounds was a limited variability due to the need for assembling each compound in a multistep synthesis de novo. The present invention overcomes this disadvantage, as it introduces not only novel helquat derivatives, but also method of preparation thereof by one-step diversification of methyl-substituted helquats using Knoevenagel condensation with substituted or non-substituted arylaldehydes.

DISCLOSURE OF THE INVENTION

The object of the present invention are helquat derivatives of the general formula I

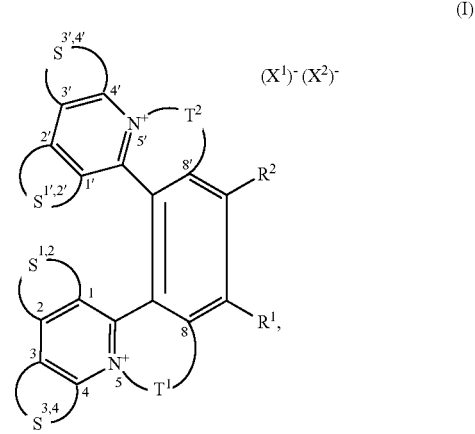

(I)

wherein substituents $R^1$ and $R^2$ are independently selected from the group comprising H and $C_1$ to $C_3$ alkyl, up to three of $S^{1,2}$, $S^{1'',2'}$, $S^{3,4}$ and $S^{3'4'}$ are present, each of $S^{1,2}$, $S^{1',2'}$, $S^{3,4}$ and $S^{3',4'}$ independently represents a linker consisting of a bivalent hydrocarbon chain having 3-6 carbon atoms, preferably hydrocarbon chain having 4 carbon atoms, more preferably hydrocarbon chain having 4 carbon atoms and two double bonds, and one or two atoms selected from the carbon atoms with the descriptor 2, 4, 2', and 4' (the carbon atom must be free of the S-linker as would be apparent to a person skilled in the art) are substituted with a substituent $R^3$ of general formula II

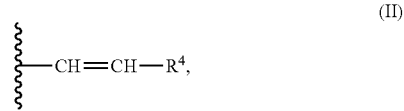

(II)

or general formula III

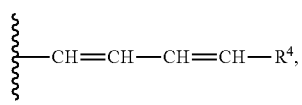

wherein R⁴ is substituted or unsubstituted aryl,
T¹ and T² are linkers that bridge atoms N⁵ with C⁸ and N⁵ with C⁸', wherein T¹ and T² independently represent a bivalent hydrocarbon chain having 2-5 carbon atoms, preferably 2 or 3 carbon atoms,
wherein
aryl is a hydrocarbon group containing 6 to 16 carbon atoms, preferably 6 to 12 carbon atoms, and at least one aromatic ring, wherein the aryl can be unsubstituted or substituted with 1 to 5 substituents, selected from a group comprising $C_1$ to $C_6$ alkyl, $C_1$ to $C_6$ halogenoalkyl, $C_1$ to $C_{12}$ alkoxy, $C_6$ to $C_{16}$ aryloxy, benzyloxy, $C_1$ to $C_6$ alkylthio, arylthio, halogeno, —OH, —SH, —NH₂, $C_1$ to $C_6$ alkylamino, arylamino, $C_1$ to $C_6$ acylamino, —CN, nitro, and —$COOR_n$, wherein $R_n$ is hydrogen or $C_1$ to $C_6$ alkyl or $C_6$ to $C_{16}$ aryl; and anions $(X^1)^-$ and $(X^2)^-$ independently represent anions of pharmaceutically acceptable salts of general formula I.

Pharmaceutically acceptable salts include salts with alkali metals, salts with inorganic or organic anions, and further salts suitable for physiological application.

The pharmaceutically acceptable salts of compounds of general formula I may be salts with anions derived from inorganic or organic acids. A person skilled in the art would be able to determine which salts are pharmaceutically acceptable, in particular salts having one or more physical properties such as enhanced pharmaceutical stability in differing temperatures and humidities, a desirable solubility in water or oil, or non-toxicity.

Suitable pharmaceutically acceptable salts of the compounds of the present invention in particular include anions derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, pamoate, methanesulfonate, ethanesulfonate, benzenesulfonate, pantothenate, toluenesulfonate, 2-hydroxyethanesulfonate, sufanilate, cyclohexylaminosulfonate, 13-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

The object of the invention are also helquat derivatives of the following formulae:

(rac)-(E)-13-(4-(dimethylamino)styryl)-6,7-dimethyl-4,5,8, 9-tetrahydroisoquinolino-[1,2-a]pyrido[1,2-k][2,9] phenanthroline-3,10-diium trifluoromethanesulfonate, i.e. (rac)-1,
(M)-(E)-13-(4-(dimethylamino)styryl)-6,7-dimethyl-4,5,8, 9-tetrahydroisoquinolino-[1,2-a]pyrido[1,2-k][2,9] phenanthroline-3,10-diium trifluoromethanesulfonate, i.e. (M)-1,
(P)-(E)-13-(4-(dimethylamino)styryl)-6,7-dimethyl-4,5,8,9-tetrahydroisoquinolino-[1,2-a]pyrido[1,2-k][2,9]phenanthroline-3,10-diium trifluoromethanesulfonate, i.e. (P)-1,
(rac)-(E)-13-(2-(6-methoxynaphthalene-2-yl)vinyl)-6,7-dimethyl-4,5,8,9-tetrahydroiso-quinolino-1,2-a]pyrido[1,2-k][2,9]phenanthroline-3,10-diium trifluoromethanesulfonate, i.e. (rac)-7,
(M)-(E)-13-(2-(6-methoxynaphthalene-2-yl)vinyl)-6,7-dimethyl-4,5,8,9-tetrahydroisoquinolino-[1,2-a]pyrido[1,2-k][2,9]phenanthroline-3,10-diium trifluoromethanesulfonate, i.e. (M)-7,
(P)-(E)-13-(2-(6-methoxynaphthalene-2-yl)vinyl)-6,7-dimethyl-4,5,8,9-tetrahydroisoquinolino-[1,2-a]pyrido[1,2-k][2,9]phenanthroline-3,10-diium trifluoromethanesulfonate, i.e. (P)-7,
(rac)-(E)-11-(2-(1,2,3,5,6,7-hexahydropyrido[3,2,1-ij] quinoline-9-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. (rac)-12,
(rac)-(E)-13-(2-(1,2,3,5,6,7-hexahydropyrido[3,2,1-ij] quinoline-9-yl)vinyl)-4,5,8,9-tetrahydro-isoquinolino[2, 1-k]pyrido[2,1-a][2,9]phenanthroline-3,10-diium trifluoromethanesulfonate, i.e. (rac)-20,
(rac)-(E)-19-(2-(1,2,3,5,6,7-hexahydropyrido[3,2,1-ij] quinoline-9-yl)vinyl)-8,9,10,13,14,15-hexahydropyrido [1''¹,2''':1'',2'']azepino[4'',3'':5',6']benzo[1',2':3,4]-azepino[2,1-a]isoquinoline-7,16-diium trifluoromethanesulfonate, i.e. (rac)-25,
2-((1E,3E)-4-(4-(dimethylamino)phenyl)buta-1,3-dien-1-yl)-6,7,10,11-tetrahydrodipyrido[2,1-a:1',2'-k][2,9] phenanthroline-5,12-diium trifluoromethanesulfonate, i.e. 30,
(M)-(E)-13-(4-methoxystyryl)-6,7-dimethyl-4,5,8,9-tetrahydroisoquinolino[1,2-a]pyrido-[1,2-k][2,9]phenanthroline-3,10-diium trifluoromethansulfonate, i.e. (M)-6,
(rac)-4,15-bis((E)-4-(dimethylamino)styryl)-6,7,8,11,12,13-hexahydrodipyrido-[1,2-a:1',2'-a']benzo[2,1-c: 3,4-c'] bisazepinediium trifluoromethanesulfonate, i.e. (rac)-41.

Furthermore, object of the invention are helquat derivatives of general formula I according to this invention for use as medicaments.

Another object of the invention are helquat derivatives of general formula I according to this invention for use as medicaments in the treatment of diseases related to increased cellular proliferation.

A further object of the invention are helquat derivatives of general formula I according to this invention for use in the treatment of oncologic diseases.

Another object of the invention is a method of preparation of helquat derivatives of general formula I according to this invention, in which a starting helquat bearing reactive methyl group, corresponding to helquat of general formula I wherein R³ is methyl and other substituents are as described above, is reacted with substituted or unsubstituted arylaldehyde which can be R⁴—CHO or R⁴—CH=CH—CHO in the presence of a base, preferably pyrrolidine or piperidine, and in an organic solvent, and the resulting product is isolated by precipitation from the solution.

In a preferred embodiment of the method of preparation, a solvent, selected from a group comprising methanol, ethanol, acetonitrile, dimethylsulfoxide and dimethylformamide, is used as the organic solvent.

A further object of the invention is a pharmaceutical agent, containing at least one helquat derivative of general formula I according to this invention or its pharmaceutically acceptable salt.

Yet another object of the invention is a pharmaceutical agent, containing at least one helquat derivative of general formula I according to this invention or its pharmaceutically acceptable salt as an active ingredient and optionally at least one pharmaceutically acceptable carrier, filler, or diluent.

A further object of the invention is a pharmaceutical agent, containing at least one helquat derivative of general formula I according to this invention or its pharmaceutically acceptable salt as an active ingredient, for use in the treatment of diseases related to increased cellular proliferation.

Another object of the present invention is use of helquat derivatives of general formula I according to this invention or their pharmaceutically acceptable salts for the preparation of a medicament for the treatment of diseases related to increased cellular proliferation.

Yet another object of the present invention is use of helquat derivatives of general formula I according to this invention or their pharmaceutically acceptable salts for the preparation of a medicament for the treatment of oncologic diseases.

Currently, there are various clinically used cytostatics. However, therapeutic results in the treatment of patients with malignant disease still remain unsatisfactory and require further search for novel more efficient compounds with lower toxicity against normal, healthy cells, which have a lower ability to induce resistance of the target cells. Therefore, apart from the search for new treatment modalities, the development of compounds targeted at cells with increased proliferation continues to be very important. Compounds with a wide spectrum of activities and a high selectivity index, e.g., against cancer cells, and exhibiting fewer undesired side effects after application are sought. From a commercial point of view, easy preparation/synthesis of such compounds (e.g., helquat derivatives) is important. Their isolation can be performed without the need for using chromatography, which is particularly advantageous from the industrial point of view.

In tests with six model cancer cell lines, the newly prepared helquat derivatives showed considerable reduction of viability (proliferation) of the cells, while cytotoxicity of these compounds against two non-cancer cell lines was significantly lower or was not detectable at all, see Table 1. Sensitivity of the individual cell lines depended on the cell type; a higher effect on faster proliferating leukemic cell line as opposed to cell lines derived from selected types of solid tumors, was proved.

In this invention, we regarded the helquats to be selectively toxic against cancer cell lines if they effected 50% decrease of metabolic activity (proliferation) of the treated cells in concentration up to 50 µmol·l$^{-1}$ (i.e. IC$_{50}$<50 µmol·l$^{-1}$). Helquats showing IC$_{50}$ higher than 150 µmol·l$^{-1}$ for a given cell line were classified as non-toxic for that cell line. Efficient growth inhibition of the cancer cell lines was assessed in micromolar concentrations, even though only a minimal effect on normal cells was detected. Therefore, helquats are useful as selective therapeutics for treatment of hyperproliferation of mammalian cells or as antimitotic and apototic drugs, mainly in anticancer therapy.

EXAMPLES

The invention is hereinafter illustrated by the following examples, which should not be construed as further limiting.

The numerical values of chemical shifts in NMR spectra are given in ppm.

Notation used in the NMR spectra: s (singlet), d (dublet), t (triplet), q (quartet), m (multiplet), b (broad signal, e.g., bdt denotes broad dublet of triplets).

Abbreviations in description of infrared spectra (IR): sh (shoulder in absorption band).

The following abbreviations describe intensity of IR spectra bands vs (very strong), s (strong), m (medium), w (weak), vw (very weak).

Where the signal assignments in the NMR spectra are indicated, the numbering scheme used in the corresponding structural formula is arbitrary.

List of Abbreviations

ESI electrospray m.p. melting point

TfO$^-$ trifluoromethanesulfonate anion

PBS phosphate buffered saline

EDTA ethylenediaminetetraacetic acid

ATP adenosine triphosphate

I. Synthesis of Compounds

Structures A to I of starting helquats are as follows:

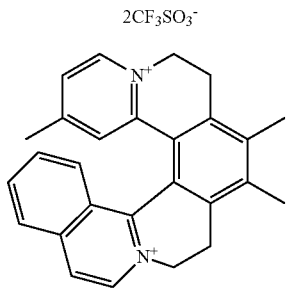

A

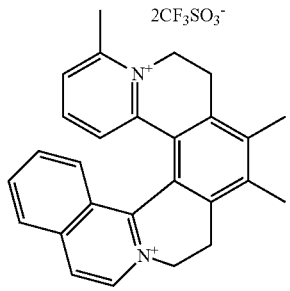

B

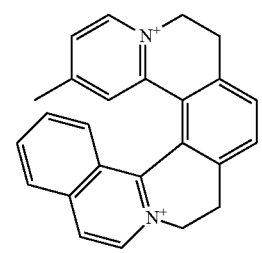

C

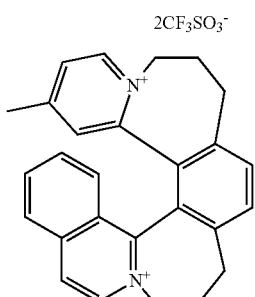

2CF₃SO₃⁻

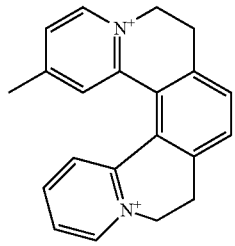

2CF₃SO₃⁻

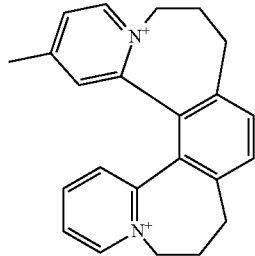

2CF₃SO₃⁻

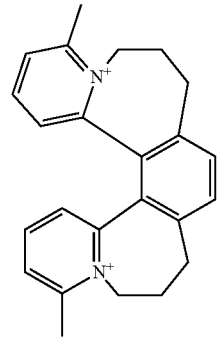

2CF₃SO₃⁻

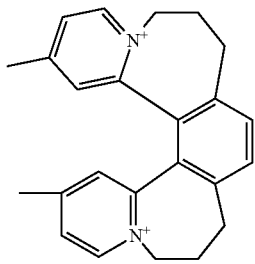

2CF₃SO₃⁻

D

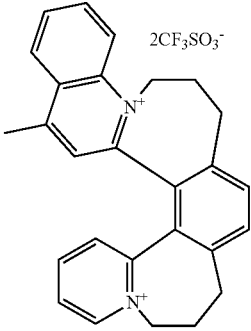

2CF₃SO₃⁻

E

Example 1

Preparation of (rac)-(E)-13-(4-(dimethylamino)styryl)-6,7-dimethyl-4,5,8,9-tetrahydroiso-quinolino[1,2-a]pyrido[1,2-k][2,9]phenanthroline-3,10-diium trifluoromethanesulfonate, i.e. (rac)-1

Starting racemic helquat A (144 mg, 0.213 mmol), 4-dimethylaminobenzaldehyde (41 mg, 0.275 mmol), pyrrolidine (0.20 ml, 2.44 mmol), and dry methanol (2.5 ml) were placed into a 10 ml flask and the resulting mixture was stirred under argon for 5 h at room temperature. Progress of the reaction was monitored by thin layer chromatography. Crude product was precipitated from the reaction mixture by addition of diethylether (90 ml). The suspension was centrifuged and the liquid was separated from the solid pellet. The solids were dissolved in methanol (5 ml) and the pure product was precipitated by addition of diethylether (40 ml). Then, centrifugation of this suspension, removal of the liquid, and drying of the solid product under vacuum of an oil pump led to 121 mg (0.150 mmol, 70% yield) of Knoevenagel condensation (rac)-1 as a dark red crystalline compound.

m.p.=269° C. (decomposition). ¹H NMR (600 MHz, acetone-$d_6$): 2.62 (s, 3H, H-34); 2.63 (s, 3H, H-35); 3.10 (s, 6H, H-33); 3.36 (ddd, J=5.2; 14.4; 16.9 Hz, 1H, H-15a); 3.45 (bdt, J=3.5; 16.0; 16.6 Hz, 1H, H-8a); 3.78 (ddd, J=1.9; 3.6; 16.9 Hz, 1H, H-8b); 3.78 (ddd, J=1.9; 3.5; 16.9 Hz, 1H, H-15b); 5.14 (dt, J=3.5; 14.0; 14.0 Hz, 1H, H-16a); 5.20 (ddd, J=1.9; 5.2; 13.5 Hz, 1H, H-16b); 5.22 (bdt, J=3.5; 14.7; 14.7 Hz, 1H, H-7a); 5.38 (ddd, J=1.9; 3.6; 14.0 Hz, 1H, H-7b); 6.59 (d, J=16.0 Hz, 1H, H-27); 6.74-6.76 (m, 2H, H-31); 7.19 (d, J=16.0 Hz, 1H, H-28); 7.25 (d, J=2.0 Hz, 1H, H-5); 7.42-7.45 (m, 2H, H-30); 7.74 (dd, 2.0; 6.7 Hz, 1H, H-3); 7.79 (ddd, J=1.3; 6.9; 8.7 Hz, 1H, H-22); 7.96 (ddd, J=1.1; 6.9; 8.11 Hz, 1H, H-21); 8.12 (dq, J=1.0; 1.0; 1.0; 8.7 Hz, 1H, H-23); 8.20 (bdt, 0.7; 0.7; 1.3; 8.1 Hz, 1H, H-20); 8.55 (bd, J=6.7 Hz, 1H, H-19); 8.77 (d, J=6.7 Hz, 1H, H-2); 9.09 (d, J=6.7 Hz, 1H, H-18). $^{13}$C NMR (151 MHz, acetone-d$_6$): 16.95 (C-35), 16.97 (C-34), 26.44 (C-15), 26.72 (C-8), 40.12 (C-33), 54.02 (C-16), 56.32 (C-7), 112.70 (C-31), 117.10 (C-27), 119.96 (C-3), 123.49 (C-29), 123.53 (C-10), 125.25 (C-19), 125.99 (C-5), 126.90 (C-11), 128.40 (C-26), 128.93 (C-23), 128.97 (C-20), 131.43 (C-30), 132.55 (C-22), 136.18 (C-21), 137.82 (C-13), 138.68 (C-18), 139.77 (C-25), 140.75 (C-14), 142.23 (C-9), 142.28 (C-12), 143.25 (C-28), 144.85 (C-2), 146.83 (C-6), 151.97 (C-24), 153.38 (C-32), 154.83 (C-4). IČ (KBr): ν (cm$^{-1}$) 517 m, 573 w, 637 s, 678 vw, 755 w, 819 w, 889 vw, 944 w, 1030 s, 1110 m, 1162 s, 1187 m, 1224 m, 1260 vs, 1275 vs sh, 1371 m, 1412 w, 1428 s, 1434 w, 1508 m, 1550 m, 1576 vs, 1630 m, 2807 vw. HRMS (ESI) m/z: [(M-CF$_3$SO$_3^-$)$^+$] (C$_{37}$H$_{35}$F$_3$N$_3$O$_3$S) calculated: 658.2346. found: 658.2343; [(M-2CF$_3$SO$_3^-$)$^{2+}$] (C$_{36}$H$_{35}$N$_3$) calculated: 254.6410. found: 254.6410.

Example 2

Preparation of (rac)-(E)-13-(2-(6-methoxynaphthalene-2-yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. (rac)-7

Starting racemic helquat A (58 mg, 0.085 mmol), 6-methoxy-2-naphtaldehyde (20 mg, 0.110 mmol), pyrrolidine (0.080 ml, 0.958 mmol), and dry methanol (1 ml) were placed into a flask and the mixture was stirred under argon for 20 h at room temperature. The reaction progress was monitored by thin layer chromatography. Crude product was isolated by a method analogous to that described in Example 1. This led to 45 mg (0.053 mmol, 62% yield) of Knoevenagel condensation product (rac)-7 as an orange crystalline solid.

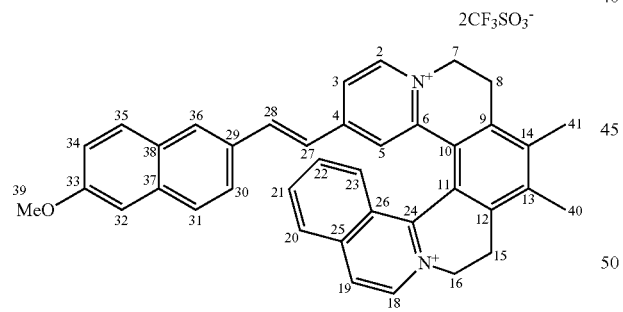

$^1$H NMR (600 MHz, acetonitriled$_3$): 2.44 (s, 3H, H-40), 2.45 (s, 3H, H-41), 3.05 (ddd, J=5.0; 14.2; 17.1 Hz, 1H, H-15a), 3.15 (bdt, J=4.6; 15.5; 15.5 Hz, 1H, H-8a), 3.50 (ddd, J=1.9; 3.5; 16.8 Hz, 1H, H-8b), 3.53 (ddd, J=1.8; 3.8; 17.1 Hz, 1H, H-15b), 3.93 (s, 3H, H-39), 4.80 (ddd, J=3.8; 13.6; 14.2 Hz, 1H, H-16a), 4.88 (ddd, J=1.8; 5.0; 13.6 Hz, 1H, H-16b), 4.93 (ddd, J=3.5; 14.0; 14.7 Hz, 1H, H-7a), 5.07 (ddd, J=1.9; 4.6; 14.0 Hz, 1H, H-7b), 6.73 (d, J=16.3 Hz, 1H, H-27), 6.94 (d, J=2.0 Hz, 1H, H-5), 7.07 (d, J=16.3 Hz, 1H, H-28), 7.22 (dd, J=2.6; 8.8 Hz, 1H, H-34), 7.29 (d, J=2.6 Hz, 1H, H-32), 7.54 (d, J=1.8; 8.6 Hz, 1H, H-30), 7.57 (dd, J=2.0; 6.6 Hz, 1H, H-3), 7.60 (ddd, J=1.2; 6.9; 8.8 Hz, 1H, H-22), 7.74 (bd, J=8.6 Hz, 1H, H-31), 7.75 (dq, J=0.9; 0.9; 0.9; 8.8 Hz, 1H, H-23), 7.82 (ddd, J=1.1; 6.9; 8.2 Hz, 1H, H-21), 7.83 (d, J=1.8 Hz, 1H, H-36), 7.84 (d, J=8.8 Hz, 1H, H-35), 7.99 (ddt, J=0.7; 0.7; 1.2; 8.2 Hz, 1H, H-20), 8.31 (dd, J=0.6; 6.7 Hz, 1H, H-19), 8.49 (d, J=6.6 Hz, 1H, H-2), 8.71 (d, J=6.7 Hz, 1H, H-18).

$^{13}$C NMR (151 MHz, acetonitriled$_3$): 17.13 (C-40), 17.21 (C-41), 26.12 (C-15), 26.65 (C-8), 54.61 (C-16), 56.18 (C-7), 56.29 (C-39), 107.27 (C-32), 120.60 (C-34), 121.44 (C-3), 121.94 (C-27), 123.33 (C-10), 125.03 (C-30), 125.49 (C-19), 126.57 (C-5), 126.88 (C-26), 127.82 (C-11), 128.64 (C-31), 128.73 (C-23), 129.01 (C-20), 129.53 (C-38), 131.09 (C-29), 131.09 (C-36), 131.32 (C-35), 132.80 (C-22), 136.50 (C-21), 137.02 (C-37), 137.51 (C-18), 138.64 (C-13), 139.78 (C-25), 141.44 (C-14), 142.25 (C-28), 142.33 (C-12), 142.70 (C-9), 145.54 (C-2), 147.32 (C-6), 151.75 (C-24), 153.89 (C-3), 160.34 (C-33).

IČ (KBr): ν (cm$^{-1}$) 518 m, 573 w, 638 s, 679 vw, 818 w, 755 w, 980 w, 1030 s, 1117 w, 1164 s, 1224 m, 1265 vs, 1352 w, 1381 w, 1393 w, 1411 vw, 1439 w, 1484 m, 1508 w, 1552 w, 1573 w, 1602 s, 1629 m, 2843 vw.

HRMS (ESI) [(M-CF$_3$SO$_3^-$)$^+$] (C$_{40}$H$_{34}$F$_3$N$_2$O$_4$S) calculated: 695.2186. found: 695.2181; [(M-2CF$_3$SO$_3^-$)$^{2+}$] (C$_{39}$H$_{34}$N$_2$O) calculated: 273.1330. found: 273.1330.

Example 3

Preparation of 2-((1E,3E)-4-(1,2,3,5,6,7-hexahydropyrido[3,2,1-ij]quinolin-9-yl)buta-1,3-dien-1-yl)-6,7,10,11-tetrahydrodipyrido[2,1-a:1',2'-k][2,9]phenanthroline-5,12-diium trifluoromethanesulfonate Starting helquat E (23 mg, 0.038 mmol), (E)-3-(1,2,3,5,6,7-hexahydropyrido[3,2,1-ij]quinoline-9-yl)acrylaldehyde (17 mg, 0.076 mmol), pyrrolidine (0.038 ml, 0.454 mmol), and dry methanol (4 ml) were placed into a flask and the mixture was stirred under argon for 1 h at room temperature. The reaction progress was monitored by thin layer chromatography. Crude product was isolated by a method analogous to that described in Example 1. This led to 23 mg (0.029 mmol, 76% yield) of Knoevenagel condensation product 31 as a dark blue solid.

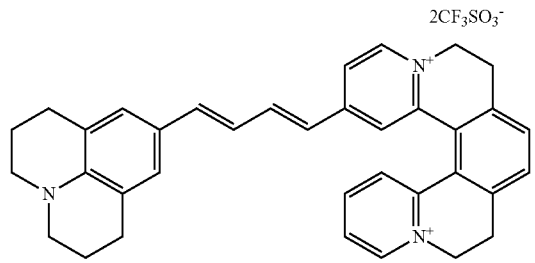 [SMILES: C(/C=C/c1cc[n+]2c(c1)-c1c(ccc3c1-c1cccc[n+]1CC3)CC2)=C\c1cc2c3c(c1)CCCN3CCC2]

$^1$H NMR (400 MHz, acetonitriled$_3$): 1.86-1.96 (m, 4H), 2.69 (t, J=6.3 Hz, 4H), 3.21-3.34 (m, 8H), 4.49-4.98 (m, 4H), 6.33 (d, J=15.2 Hz, 1H), 6.70-6.84 (m, 2H), 6.98 (s, 2H), 7.29 (dd, J=10.0, 15.2 Hz, 1H), 7.55 (d, J=1.9 Hz, 1H), 7.68-7.74 (m, 3H), 7.87-7.92 (m, 1H), 8.00-8.04 (m, 1H), 8.15-8.21 (m, 1H), 8.40 (d, J=6.8 Hz, 1H), 8.80-8.84 (m, 1H). Elem. analysis: C$_{38}$H$_{35}$F$_6$N$_3$O$_6$S$_2$, calculated: C (56.50), H (4.37), N (5.20). found: C (56.50), H (4.21), N (4.99).

Example 4

Preparation of (rac)-(E)-11-(2-(1,2,3,5,6,7-hexahydropyrido[3,2,1-ij]yl)vinyl)-6,7-dimethyl-4,5,8,9-tetrahydroisoquinolino[1,2-a]pyrido[1,2-k][2,9]phenanthroline-3,10-diium trifluoromethanesulfonate, i.e. (rac)-12

Racemic helquat B (70 mg, 0.103 mmol), 9-julolidinecarbaldehyde (147 mg, 0.725 mmol), pyrrolidine (0.100 ml), and dry methanol (7 ml) were placed into a flask and the mixture was stirred under argon for 2.5 h at room temperature. The reaction progress was monitored by thin layer chromatography. Crude product was isolated by a method analogous to that described in Example 1. This led to 41 mg (0.048 mmol, 47% yield) of Knoevenagel condensation product 12 as a violet crystalline solid.

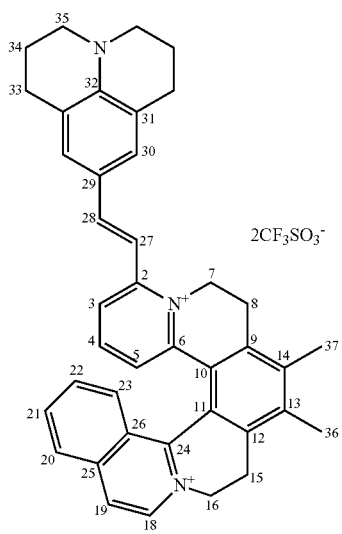 [SMILES: Cc1c(C)c2c(c3c1CC[n+]1ccc4ccccc4c1-3)-c1cccc(/C=C/c3cc4c5c(c3)CCCN5CCC4)[n+]1CC2]

$^1$H NMR (600 MHz, acetone-$d_6$): 1.98-2.03 (m, 4H, H-34); 2.65 (s, 3H, H-36); 2.66 (s, 3H, H-37); 2.79-2.83 (m, 4H, H-33); 3.30 (bddd, 1H, J=3.7, 14.2, 17.0 Hz, H-8a); 3.38-3.41 (m, 4H, H-35); 3.47 (bddd, 1H, J=3.7, 14.5, 17.0 Hz, H-15a); 3.80 (ddd, 1H, J=1.9, 4.7, 17.0 Hz, H-15b); 3.82 (ddd, 1H, J=1.9, 4.9, 17.0 Hz, H-8b); 5.04 (dt, 1H, J=3.7, 14.0, 14.0 Hz, H-7a); 5.16 (dt, 1H, J=3.7, 14.3, 14.3 Hz, H-16a); 5.39 (ddd, 1H, J=1.9, 4.7, 14.0 Hz, H-16b); 5.60 (ddd, 1H, J=1.9, 4.9, 13.8 Hz, H-7b); 7.20 (dd, 1H, J=1.2, 8.0 Hz, H-5); 7.34 (s, 2H, H-30); 7.55 (t, 1H, J=8.1 Hz, H-4); 7.73 (d, 1H, J=15.5 Hz, H-28); 7.82 (ddd, 1H, J=1.2, 6.9, 8.8 Hz, H-22); 7.84 (d, 1H, J=15.5 Hz, H-27); 7.98 (ddd, 1H, J=1.1, 6.9, 8.1 Hz, H-21); 8.01 (dd, 1H, J=1.2, 8.2 Hz, H-3); 8.11 (dq, 1H, J=0.9, 0.9, 0.9, 8.8 Hz, H-23); 8.28 (bd, 1H, J=8.1 Hz, H-20); 8.53 (bd, 1H, J=6.8 Hz, H-19); 9.02 (d, 1H, J=6.8 Hz, H-18). $^{13}$C NMR (151 MHz, acetone-$d_6$): 16.74 (C-36); 16.85 (C-37); 22.14 (C-34); 26.19 (C-8); 26.81 (C-15); 28.30 (C-33); 49.63 (C-7); 50.60 (C-35); 56.16 (C-16); 110.09 (C-27); 122.07 (C-31); 122.50 (C-29); 123.55 (C-13); 123.83 (C-3); 125.62 (C-19); 126.86 (C-5); 126.92 (C-26); 128.78 (C-23); 129.08 (C-20); 129.36 (C-14); 129.65 (C-30); 132.50 (C-22); 136.05 (C-21); 137.36 (C-18); 138.56 (C-9); 139.80 (C-25); 140.25 (C-12); 141.65 (C-10); 141.91 (C-4); 142.22 (C-11); 146.96 (C-32); 147.10 (C-28); 147.33 (C-6); 151.96 (C-24); 156.03 (C-2).

IČ (KBr): ν (cm$^{-1}$) 517 m, 573 w, 638 s, 1030 vs, 1163 w, 1484 m, 1524 w, 1553 s, 1588 w, 1627 b, 3074 w.

HRMS (ESI) m/z: [(M-CF$_3$SO$_3^-$)$^+$] (C$_{41}$H$_{39}$F$_3$N$_3$O$_3$S) calculated: 710.2659. found: 710.2653.

Elem. analysis: C$_{42}$H$_{39}$F$_6$N$_3$O$_6$S$_2$, calculated: C (58.66), H (4.57), F (13.26), N (4.89), S (7.46). found: C (58.42), H (5.08), F (12.92), N (4.40), S (7.18).

Example 5

Preparation of (rac)-4,15-bis((E)-4-(dimethylamino)styryl)-6,7,8,11,12,13-hexahydro-dipyrido[1,2-a:1',2'-a']benzo[2,1-c:3,4-c']bisazepinediium trifluoromethanesulfonate, i.e. (rac)-41

Racemic helquat G (60 mg, 0.094 mmol), 4-(dimethylamino)benzaldehyde (174 mg, 1.17 mmol), piperidine (0.111 ml, 1.12 mmol), and dry methanol (2 ml) were placed into a flask and the mixture was stirred under argon for 72 h at room temperature. The reaction progress was monitored by thin layer chromatography. Crude product was isolated by a method analogous to that described in Example 1. This led to 79 mg (0.088 mmol, 94% yield) of Knoevenagel condensation product (rac)-41 as a dark red crystalline solid.

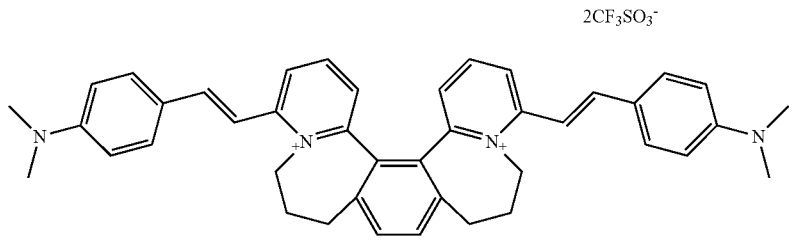

m.p.=318-322° C. $^1$H NMR (400 MHz, acetonitrile-$d_3$): 2.32-2.38 (m, 2H), 2.41-2.49 (m, 2H), 2.69-2.76 (m, 2H), 3.00-3.06 (m, 2H), 3.07 (s, 12H), 4.29 (dt, J=5.2; 14.0 Hz, 2H), 5.01 (dd, J=5.7; 14.5 Hz, 2H), 6.81-6.83 (m, 4H), 6.95 (dd, J=1.2; 7.7; Hz, 2H), 7.18 (d, J=15.5 Hz, 2H), 7.67 (s, 2H), 7.70-7.79 (m, 6H), 7.92 (t, J=8.1 Hz, 2H), 8.16 (dd, J=1.1; 8.5 Hz, 2H). MS (ESI) m/z (%): 753 (10), 302 (100). HRMS (ESI) m/z: [M-CF$_3$SO$_3^-$)$^+$](C$_{43}$H$_{44}$F$_3$N$_4$O$_3$S) calculated: 753.3081. found: 753.3073. Elem. analysis: C$_{44}$H$_{44}$F$_6$N$_4$O$_6$S$_2$, calculated: C (58.53), H (4.91), N (6.20), F (12.62), S (7.10). found: C (58.83), H (4.84), N (5.91), F (12.22), S (7.30).

Example 6

Preparation of (M)-(E)-13-(4-(dimethylamino) styryl)-6,7-dimethyl-4,5,8,9-tetrahydroiso-quinolino[1,2-a]pyrido[1,2-k][2,9]phenanthroline-3,10-diium trifluoromethanesulfonate, i.e. (M)-1

Starting non-racemic helquat (M)-A (35 mg, 0.052 mmol), 4-dimethylaminobenzaldehyde (15 mg, 0.103 mmol), pyrrolidine (0.052 ml, 0.621 mmol), and dry methanol (1 ml) were placed into a flask and the mixture was stirred under argon for 1 h at room temperature. The reaction progress was monitored by thin layer chromatography. Crude product was isolated by a method analogous to that described in Example 1. This led to 36 mg (0.044 mmol, 85% yield) of Knoevenagel condensation product (M)-1 as a dark red crystalline solid.

m.p.=264-266° C. $^1$H NMR (600 MHz, acetone$_d6$): 2.52 (s, 3H), 2.55 (s, 3H), 3.08 (s, 6H), 3.23-3.31 (m, 1H), 3.34-3.42 (m, 1H), 3.64-3.73 (m, 2H), 5.01-5.08 (m, 1H), 5.10-5.19 (m, 2H), 5.30-5.34 (m, 1H), 6.48 (d, J=16.0 Hz, 1H), 6.70 (d, J=9.0 Hz, 2H), 7.13 (d, J=16.0 Hz, 1H), 7.15 (d, J=1.9 Hz, 1H), 7.38 (d, J=8.9 Hz, 2H), 7.66 (dd, J=1.9, 6.7 Hz, 1H), 7.70-7.74 (m, 1H), 7.87-7.91 (m, 1H), 8.00-8.03 (m, 1H), 8.12 (d, J=8.2 Hz, 1H), 8.47 (d, J=6.7 Hz, 1H), 8.69 (d, J=6.7 Hz, 1H), 9.00 (d, J=6.7 Hz, 1H). $^{13}$C NMR (151 MHz, acetone$_d6$): 16.9; 17.0; 26.3; 26.7; 40.1; 53.9; 56.2; 112.6; 117.1; 120.0; 123.4; 123.4; 125.1; 126.2; 126.7; 127.8; 128.2; 128.8; 128.9; 131.4; 132.4; 136.1; 137.8; 138.5; 139.7; 140.7; 142.1; 142.2; 143.0; 144.8; 146.7; 151.8; 153.3; 154.6. IČ (film): ν (cm$^{-1}$) 517 w, 573 w, 637 m, 757 vw, 820 w, 944 w, 975 w, br, 1030 s, 1110 m, 1159 s, 1224 m, 1255 vs, 1335 m, 1369 m, 1411 w, 1509 m, 1529 m, 1547 m, 1571 vs, 1630 w. HRMS (ESI) m/z: [(M-CF$_3$SO$_3^-$)$^+$] (C$_{37}$H$_{35}$F$_3$N$_3$O$_3$S) calculated: 658.2346. found: 658.2331.

Example 7

Preparation of (M)-(E)-13-(2-(6-methoxynaphthalene-2-yl)vinyl)-6,7-dimethyl-4,5,8,9-tetrahydroiso-quinolino[1,2-a]pyrido[1,2-k][2,9]phenanthroline-3,10-diium trifluoromethanesulfonate, i.e. (M)-7

Starting non-racemic helquat (M)-A (51 mg, 0.075 mmol), 6-methoxy-2-naphthaldehyde (57 mg, 0.301 mmol), pyrrolidine (0.188 ml, 2.256 mmol) and dry methanol (2 ml) were placed into a flask and the mixture was stirred under argon for 1 h at room temperature. The reaction progress was monitored by thin layer chromatography. Crude product was isolated by a method analogous to that described in Example 1. This led to 49 mg (0.058 mmol, 77% yield) of Knoevenagel condensation product (M)-7 as an orange crystalline solid.

$^1$H NMR (400 MHz, acetonitriled$_3$): 2.53 (s, 6H), 3.07-3.25 (m, 2H), 3.53-3.63 (m, 2H), 3.93 (s, 3H), 4.79-4.98 (m, 3H), 5.05-5.12 (m, 1H), 6.79 (d, J=16.3 Hz, 1H), 6.93 (d, J=1.8 Hz, 1H), 7.08 (d, J=16.3 Hz, 1H), 7.21-7.25 (m, 1H), 7.30 (d, J=2.4 Hz, 1H), 7.56-7.67 (m, 3H), 7.78-7.90 (m, 5H), 8.04 (d, J=8.2 Hz, 1H), 8.36 (d, J=6.7 Hz, 1H), 8.50 (d, J=6.6 Hz, 1H), 8.72 (d, J=6.7 Hz, 1H). IČ (film): ν (cm$^{-1}$) 518 w, 637 s, 756 w, 819 w, 858 w, 978 w, br, 1029 s, 1158 s, 1224 m, 1256 vs, 1352 w, 1393 w, 1434 w, 1483 m, 1509 w, 1551 w, 1573 w, 1600 s, 1628 w. HRMS (ESI) m/z: [(M-CF$_3$SO$_3^-$)$^+$] (C$_{40}$H$_{34}$F$_3$N$_2$O$_4$S) calculated: 695.2186. found: 695.2180.

Example 8

Preparation of (P)-(E)-13-(4-(dimethylamino)styryl)-6,7-dimethyl-4,5,8,9-tetrahydroiso-quinolino[1,2-a]pyrido[1,2-k][2,9]phenanthroline-3,10-diium trifluoromethanesulfonate, i.e. (P)-1

According to procedure in Example 7, reaction of 35 mg of non-racemic helquatu (P)-A and 15 mg of 4-dimethylaminobenzaldehyde gave analogously 33 mg of non-racemic derivative (P)-1 as a dark red crystalline solid (80% yield).

Example 9

(P)-(E)-13-(2-(6-methoxynaphthalene-2-yl)vinyl)-6,7-dimethyl-4,5,8,9-tetrahydroiso-quinolino[1,2-a]pyrido[1,2-k][2,9]phenanthroline-3,10-diium trifluoromethanesulfonate, i.e. (P)-7

According to procedure in Example 8, reaction of non-racemic helquat (P)-A and 6-methoxy-2-naphthaldehyde gave analogously non-racemic derivative (P)-7.

Example 10

(rac)-(E)-13-(4-(dimethylamino)styryl)-4,5,8,9-tetrahydroisoquinolino[2,1-k]pyrido[2,1-a][2,9]phenanthroline-3,10-diium trifluoromethanesulfonate

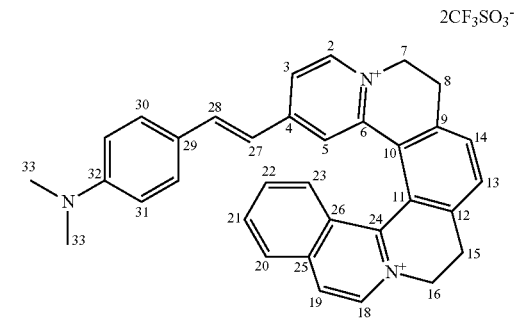 [SMILES: CN(C)c1ccc(/C=C/c2cc[n+]3c(c2)-c2c(ccc4c2-c2c5ccccc5cc[n+]2CC4)CC3)cc1]

$^1$H NMR (600 MHz, acetone-d$_6$): 3.11 (s, 6H, H-33), 3.54-3.71 (m, 4H, H-15 and H-8), 5.17-5.27 (m, 2H, H-7), 5.32-5.42 (m, 2H, H-16), 6.64 (d, J=16.0 Hz, 1H, H-27), 6.75-6.78 (m, 2H, H-31), 7.21 (d, J=16.0 Hz, 1H, H-28), 7.45 (d, J=2.1 Hz, 1H, H-5), 7.43-7.47 (m, 2H, H-30), 7.76 (dd, J=6.6, 2.1 Hz, 1H, H-3), 7.80 (ddd, J=8.8, 6.9, 1.2 Hz, 1H, H-22), 8.00 (ddd, J=8.2, 6.9, 1.1 Hz, 1H, H-21), 8.04 (bd, J=7.7 Hz, 1H, H-13), 8.06 (bd, J=7.7 Hz, 1H, H-14), 8.18 (dq, J=8.8, 3×1.0 Hz, 1H, H-23), 8.24 (ddt, J=8.2, 1.2, 0.7, 0.7 Hz, 1H, H-20), 8.63 (bd, J=6.8 Hz, 1H, H-19), 8.84 (bd, J=6.6 Hz, 1H, H-2), 9.14 (d, J=6.8 Hz, 1H, H-18).

Example 11

(rac)-(E)-19-(4-(dimethylamino)styryl)-8,9,10,13,14,15-hexahydropyrido[1''',2''':1'',2'']-azepino[4'',3'':5',6']benzo[1',2':3,4]azepino[2,1-a]isoquinoline-7,16-diium trifluoromethanesulfonate

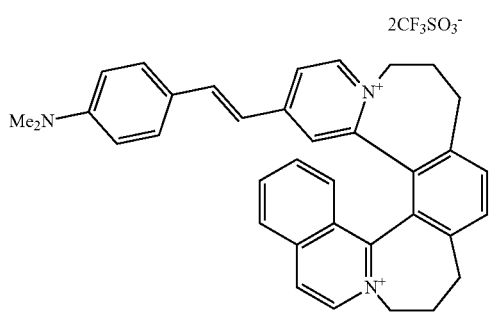 [SMILES: CN(C)c1ccc(/C=C/c2cc[n+]3c(c2)-c2c(ccc4c2-c2c5ccccc5cc[n+]2CCC4)CCC3)cc1]

$^{1}$H NMR (400 MHz, acetone-$d_6$): 2.60 (m, 2H), 2.80 (m, 4H), 3.07 (s, 6H), 3.20 (dd, J=6.8; 13.6 Hz, 2H), 4.86 (m, 1H), 4.99 (d, J=8.0 Hz, 2H), 5.30 (dd, J=5.6; 13.6 Hz, 1H), 6.75 (m, 3H), 7.04 (s, 1H), 7.47-7.52 (m, 3H), 7.84 (dd, J=2.0; 6.8 Hz, 1H), 7.93 (dt, J=0.4; 7.6 Hz, 1H), 7.98 (s, 2H), 8.02 (dd, J=0.4; 8.8 Hz, 1H), 8.10 (dt, J=0.8; 7.2 Hz, 1H), 8.30 (d, J=8.4 Hz, 1H), 8.67 (d, J=6.8 Hz, 1H), 8.71 (d, J=6.8 Hz, 1H), 9.16 (d, J=6.8 Hz, 1H).

Example 12

(rac)-(E)-11-(4-(dimethylamino)styryl)-6,7-dimethyl-4,5,8,9-tetrahydroisoquinolino[1,2-a]pyrido[1,2-k][2,9]phenanthroline-3,10-diium trifluoromethanesulfonate

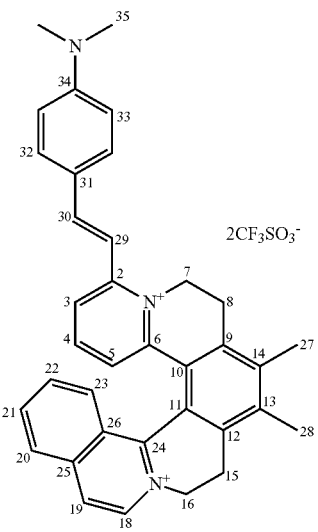 [SMILES: Cc1c(C)c2c(c3c1CC[n+]1ccc4ccccc4c1-3)-c1cccc(/C=C/c3ccc(N(C)C)cc3)[n+]1CC2]

$^{1}$H NMR (600 MHz, acetone-$d_6$): 2.66 (bs, 3H, H-27); 2.66 (bs, 3H, H-28); 3.15 (s, 61-1, H-35); 3.34 (bddd, J=4.2, 14.4, 17.3 Hz, 1H, H-8a); 3.48 (bdt, J=4.0, 16.2, 16.2 Hz, 1H, H-15a); 3.82 (bdt, J=3.7, 16.8, 16.8 Hz, 1H, H-8b); 3.82 (bdt, J=3.5, 16.8, 16.8 Hz, 1H, H-15b); 5.12 (bdt, J=3.7, 14.2, 14.2 Hz, 1H, H-7a); 5.17 (bdt, J=3.5, 14.7, 14.7 Hz, 1H, H-16a); 5.40 (bdd, J=4.0, 13.5 Hz, 1H, H-16b); 5.68 (bddd, J=1.6, 4.2, 13.3 Hz, 1H, H-7b); 6.87-6.90 (m, 2H, H-33); 7.30 (d, J=8.0 Hz, 1H, H-5); 7.63 (t, J=8.1 Hz, 1H, H-4); 7.68 (d, J=15.6 Hz, 1H, H-29); 7.77-7.80 (m, 2H, H-32); 7.82 (d, J=15.6 Hz, 1H, H-30), 7.84 (ddd, J=1.2, 7.0, 8.5 Hz, 1H, H-22); 7.99 (bdd, J=7.0, 8.2 Hz, 1H, H-21); 8.07 (bd, J=8.2 Hz, 1H, H-3); 8.13 (d, J=8.5 Hz, 1H, H-23); 8.29 (bd, J=8.2 Hz, 1H, H-20); 8.55 (bd, J=6.7 Hz, 1H, H-19); 9.04 (bd, J=6.7 Hz, 1H, H-18).

Example 13

(E)-2-(4-(dimethylamino)styryl)-6,7,10,11-tetrahydrodipyrido[2,1-a:1',2'-k][2,9]phenanthroline-5,12-diium trifluoromethanesulfonate

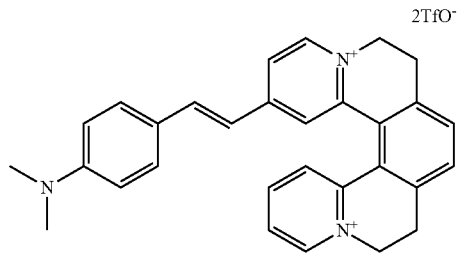 [SMILES: CN(C)c1ccc(/C=C/c2cc[n+]3c(c2)-c2c(ccc4c2-c2cccc[n+]2CC4)CC3)cc1]

$^{1}$H NMR (400 MHz, acetonitrile-$d_3$): 3.03 (s, 6H), 3.21-3.38 (m, 4H), 4.54-4.98 (m, 4H), 6.74 (d, J=9.0 Hz, 2H), 6.83 (d, J=16.0 Hz, 1H), 7.38-7.47 (m, 3H), 7.67 (d, J=1.9 Hz, 1H), 7.70 (s, 2H), 7.80 (dd, J=2.0, 6.7 Hz, 1H), 7.87-7.92 (m, 1H), 8.03-8.07 (m, 1H), 8.15-8.21 (m, 1H), 8.46 (d, J=6.8 Hz, 1H), 8.81-8.85 (m, 1H).

Example 14

(rac)-(E)-2-(4-(dimethylamino)styryl)-6,7,8,11,12,13-hexahydrodipyrido[1,2-a:1',2'-a']benzo[2,1-c:3,4-c']bisazepinediium trifluoromethanesulfonate, i.e. (rac)-35

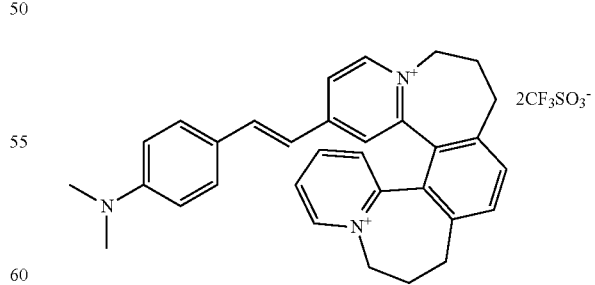

$^{1}$H NMR (400 MHz, acetone-$d_6$): 2.35-2.92 (m, 6H), 3.01-3.18 (m, 2H), 3.06 (s, 6H), 4.66 (td, J=13.3, 5.6 Hz, 1H), 4.77-5.02 (m, 2H), 5.14-5.21 (m, 1H), 6.75 (d, J=9.1 Hz, 2H), 6.95 (d, J=16.2 Hz, 1H), 7.47 (d, J=2.2 Hz, 1H), 7.52 (d, J=8.9 Hz, 2H), 7.72 (d, J=15.9 Hz, 1H), 7.84 (s, 2H), 7.93 (dd, J=8.2, 1.5 Hz, 1H), 8.18 (ddd, J=7.9, 4.3, 1.4 Hz, 2H), 8.47 (td, J=7.9, 1.5 Hz, 1H), 8.92 (d, J=6.8 Hz, 1H), 9.35 (dd, J=6.2, 1.4 Hz, 1H).

Example 15

(rac)-2,17-bis((E)-4-(dimethylamino)styryl)-6,7,8,11,12,13-hexahydrodipyrido[1,2-a:1',2'-a']benzo[2,1-c:3,4-c']bisazepinediium trifluoromethanesulfonate

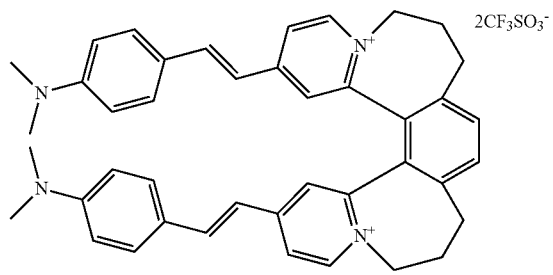 [SMILES: CN(C)c1ccc(/C=C/c2cc[n+]3c(c2)-c2c(ccc4c2-c2cc(/C=C/c5ccc(N(C)C)cc5)cc[n+]2CCC4)CCC3)cc1]

$^1$H NMR (400 MHz, acetonitriled$_3$): 2.32-2.40 (m, 2H), 2.45-2.53 (m, 2H), 2.58-2.64 (m, 2H), 2.99 (dd, J=6.9; 14.1 Hz, 2H), 3.03 (s, 12H), 4.39 (ddd, J=5.5; 13.1; 14.5 Hz, 2H), 4.62 (dd, J=6.2; 13.8 Hz, 2H), 6.74 (d, J=9.0 Hz, 4H), 6.84 (d, J=16.0 Hz, 2H), 7.00 (d, J=2.0 Hz; 2H), 7.47 (d, J=8.96 Hz, 4H), 7.51 (d, J=16.0 Hz, 2H), 7.87 (s, 2H), 7.84 (dd, J=2.0; 6.8 Hz, 2H), 8.51 (dd, J=6.8 Hz, 2H).

Example 16

(rac)-(E)-20-(4-dimethylamino)styryl)-6,7,8,11,12,13-hexahydropyrido-[1''',2'':1'',2'']azepino[4'',3'':5',6']benzo[1',2':3,4]azepino[1,2-a]quinoline-5,14-diium trifluoromethanesulfonate

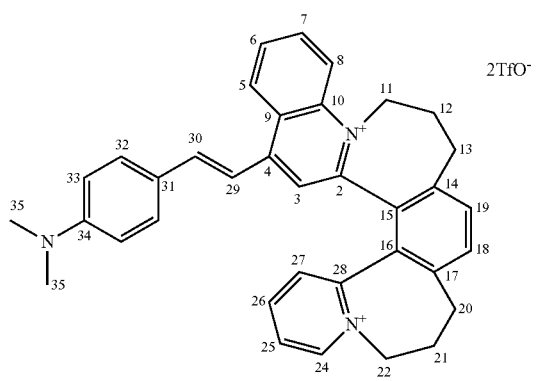 [SMILES: CN(C)c1ccc(/C=C/c2cc3[n+](c4ccccc24)CCCc2ccc4c(c2-3)-c2cccc[n+]2CCC4)cc1]

$^1$H NMR (600 MHz, acetonitrile-d$_3$): 2.37-2.43 (m, 1H, H-12a), 2.43-2.46 (m, 2H, H-20a a H-13a), 2.49-2.50 (m, 1H, H-21a), 2.69-2.76 (m, 1H, H-21b), 2.71-2.77 (m, 1H, H-12b), 3.00-3.07 (m, 2H, H-20b a H-13b), 3.07 (s, 6H, H-35), 4.44 (ddd, J=15.2, 13.5, 5.2 Hz, 1H, H-11a), 4.77 (dt, J=13.4, 13.4, 5.2 Hz, 1H, H-22a), 4.91 (bdd, J=13.6, 6.5 Hz, 1H, H-22b), 5.33 (bdd, J=15.2, 5.6 Hz, 1H, H-11b), 6.78-6.80 (m, 2H, H-33), 7.12 (s, 1H, H-3), 7.16 (d, J=15.5 Hz, 1H, H-29), 7.45 (ddd, J=8.1, 1.5, 0.6 Hz, 1H, H-27), 7.61-7.63 (m, 2H, 11-32), 7.63 (dt, J=15.5, 0.5, 0.5 Hz, 1H, H-30), 7.74 (d, J=7.8 Hz, 1H, H-18), 7.76 (d, J=7.8 Hz, 1H, H-19), 7.92 (ddd, J=8.4, 6.9, 1.0 Hz, 1H, H-6), 7.94 (ddd, J=7.8, 6.2, 1.5 Hz, 1H, H-25), 8.15 (dt, J=7.9, 7.9, 1.5 Hz, 1H, H-26), 8.19 (ddd, J=8.9, 6.9, 1.4 Hz, 1H, H-7), 8.42 (bdq, J=8.9, 3×0.7 Hz, 1H, H-8), 8.70 (bddt, J=8.4, 1.4, 0.6, 0.6 Hz, 1H, H-5), 8.96 (ddd, J=6.2, 1.5, 0.6 Hz, 1H, H-24).

Example 17

(rac)-(E)-13-(2-(1,2,3,5,6,7-hexahydropyrido[3,2,1-ij]quinolin-9-yl)vinyl)-6,7-dimethyl-4,5,8,9-tetrahydroisoquinolino[1,2-a]pyrido[1,2-k][2,9]phenanthroline-3,10-diium trifluoromethanesulfonate

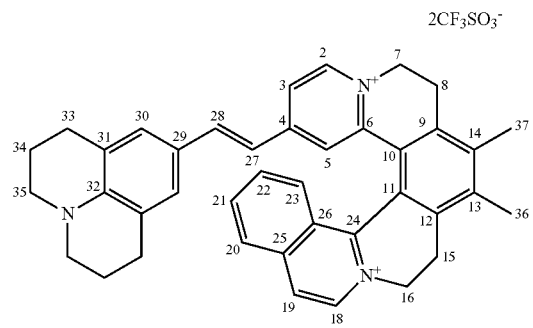 [SMILES: Cc1c(C)c2c(c3c1CC[n+]1ccc(/C=C/c4cc5c6c(c4)CCCN6CCC5)cc1-3)-c1c3ccccc3cc[n+]1CC2]

$^1$H NMR (600 MHz, acetoned$_6$): 1.93-1.98 (m, 4H, H-34); 2.61 (s, 3H, H-36); 2.63 (s, 3H, H-37); 2.70-2.76 (m, 4H, H-35); 3.33-3.36 (m, 4H, H-33); 3.35 (bdt, J=5.1, 14.5, 16.8 Hz, 1H, H-15a); 3.44 (bdt, J=4.8, 15.9, 15.9 Hz, 1H, H-8a); 3.75 (ddd, J=2.0, 3.6, 16.8 Hz, 1H, H-15b); 3.75 (ddd, J=1.9, 3.8, 16.8 Hz, 1H, H-8b); 5.09 (dt, J=3.6, 14.0, 14.0 Hz, 1H, H-16a); 5.16 (ddd, J=2.0, 5.1, 13.5 Hz, 1H, H-16b); 5.23 (dt, J=3.8, 14.8, 14.8 Hz, 1H, H-7a); 5.36 (ddd, J=1.9, 4.8, 14.0 Hz, 1H, H-7b); 6.50 (d, J=15.9 Hz, 1H, H-27); 7.00 (s, 2H, H-30); 7.11 (d, J=15.9 Hz, 1H, H-28); 7.18 (d, J=2.0 Hz, 1H, H-5); 7.65 (dd, J=2.0, 6.8 Hz, 1H, H-3); 7.80 (ddd, J=1.3, 6.9, 8.1 Hz, 1H, H-22); 7.97 (ddd, J=1.1, 6.9, 8.1 Hz, 1H, H-21); 8.13 (dq, J=0.9, 0.9, 0.9, 8.7 Hz, 1H, H-23); 8.21 (bddt, J=0.7, 0.7, 1.3, 8.1 Hz, 1H, H-20); 8.54 (bd, J=6.7 Hz, 1H, H-19); 8.70 (d, J=6.8 Hz, 1H, H-2); 9.08 (d, J=6.7 Hz, 1H, H-18).

Example 18

(rac)-(E)-13-(2-(1,2,3,5,6,7-hexahydropyrido[3,2,1-ij]quinolin-9-yl)vinyl)-4,5,8,9-tetrahydroisoquinolino[2,1-k]pyrido[2,1-a][2,9]phenanthroline-3,10-diium trifluoromethanesulfonate, i.e. (rac)-20

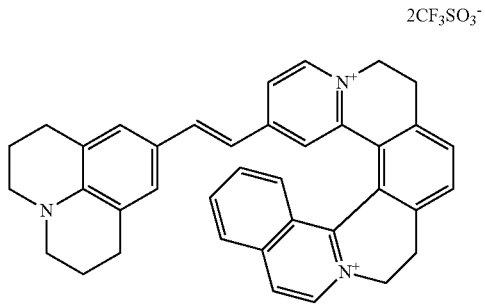 [SMILES: C(=C\c1cc[n+]2c(c1)-c1c(ccc3c1-c1c4ccccc4cc[n+]1CC3)CC2)/c1cc2c3c(c1)CCCN3CCC2]

$^1$H NMR (400 MHz, acetone-d$_6$): 1.88-1.94 (m, 4H), 2.69 (dq, J=2.0; 6.4 Hz, 4H), 3.31 (t, J=5.6 Hz, 4H), 3.52-3.61 (m, 4H), 5.06-5.13 (m, 2H), 5.24 (dt, J=4.8; 13.6 Hz, 1H), 5.31-5.36 (m, 1H), 6.46 (d, J=16.0 Hz, 1H), 6.95 (s, 2H), 7.05 (d, J=16.0 Hz, 1H), 7.26 (s, 1H), 7.64 (d, J=6.8 Hz, 1H), 7.76 (t, J=7.6 Hz, 1H), 7.95 (t, J=7.6 Hz, 1H), 7.99 (s, 2H), 8.14 (d, J=8.8 Hz, 1H), 8.20 (d, J=8.4 Hz, 1H), 8.58 (d, J=6.8 Hz, 1H), 8.70 (d, J=6.8 Hz, 1H), 9.09 (d, J=6.8 Hz, 1H).

Example 19

(rac)-(E)-19-(2-(1,2,3,5,6,7-hexahydropyrido[3,2,1-ij]quinolin-9-yl)vinyl)-8,9,10,13,14,15-hexahydropyrido[1''',2''':1'',2'']azepino[4'',3'':5',6']benzo[1',2':3,4]azepino[2,1-a]isoquinoline-7,16-diium trifluoromethanesulfonate, i.e. (rac)-25

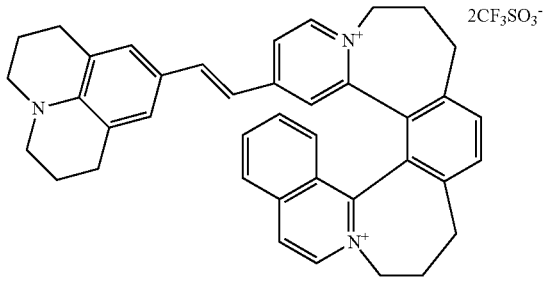 [SMILES: C(=C\c1cc[n+]2c(c1)-c1c(ccc3c1-c1c4ccccc4cc[n+]1CCC3)CCC2)/c1cc2c3c(c1)CCCN3CCC2]

$^1$H NMR (400 MHz, acetone-d$_6$): 1.91 (m, 4H), 2.58 (m, 2H), 2.69 (t, J=6.0 Hz, 4H), 2.84 (m, 4H), 3.18 (dd, J=1.6; 7.2 Hz, 1H), 3.21 (dd, J=2.0; 6.0 Hz, 1H), 3.32 (t, J=5.6 Hz, 4H), 4.84 (dt, J=5.6; 13.6 Hz, 1H), 4.94 (dd, J=3.2; 9.2 Hz, 2H), 5.30 (dd, J=5.6; 14.0 Hz, 1H), 6.62 (d, J=16.0 Hz, 1H), 6.95 (dd, J=2.0 Hz, 1H), 7.03 (s, 2H), 7.36 (d, J=16.0 Hz, 1H), 7.72 (dd, J=2.0; 6.8 Hz, 1H), 7.93 (dt, J=1.2; 6.8 Hz, 1H), 7.97 (s, 2H), 8.02 (dd, J=0.8; 8.4 Hz, 1H), 8.11 (dt, J=1.2; 6.8 Hz, 1H), 8.31 (d, J=8.4 Hz, 1H), 8.60 (d, J=6.8 Hz, 1H), 8.68 (d, J=6.8 Hz, 1H), 9.16 (d, J=6.8 Hz, 1H).

Example 20

(E)-2-(2-(1,2,3,5,6,7-hexahydropyrido[3,2,1-ij]quinoline-9-yl)vinyl)-6,7,10,11-tetrahydro-dipyrido[2,1-a:1',2'-k][2,9]phenanthroline-5,12-diium trifluoromethanesulfonate

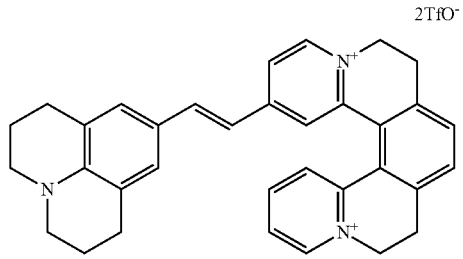 [SMILES: C(=C\c1cc[n+]2c(c1)-c1c(ccc3c1-c1cccc[n+]1CC3)CC2)/c1cc2c3c(c1)CCCN3CCC2]

$^1$H NMR (400 MHz, acetonitrile-d$_3$): 1.86-1.94 (m, 4H), 2.69 (t, J=6.3 Hz, 4H), 3.21-3.34 (m, 8H), 4.49-4.97 (m, 4H), 6.69 (d, J=15.9 Hz, 1H), 6.99 (s, 2H), 7.29 (d, J=15.9 Hz, 1H), 7.56 (d, J=2.0 Hz, 1H), 7.68-7.71 (m, 3H), 7.86-7.92 (m, 1H), 8.02-8.06 (m, 1H), 8.14-8.20 (m, 1H), 8.36 (d, J=6.8 Hz, 1H), 8.80 (m, 1H).

Example 21

(rac)-(E)-2-(2-(1,2,3,5,6,7-hexahydropyrido[3,2,1-ij]quinoline-9-yl)vinyl)-6,7,8,11,12,13-hexahydrodipyrido[1,2-a:1',2'-a']benzo[2,1-c:3,4-c']bisazepinediium trifluoromethanesulfonate

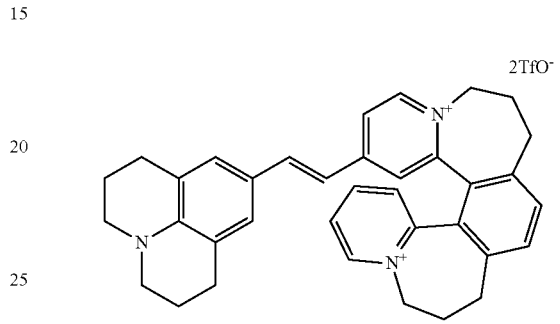

$^1$H NMR (400 MHz, acetone-d$_6$): 1.84-1.97 (m, 4H), 2.37-2.94 (m, 10H), 3.03-3.21 (m, 2H), 3.28-3.35 (m, 4H), 4.54-4.67 (m, 1H), 4.78-4.95 (m, 2H), 5.18 (dd, J=13.7, 6.4 Hz, 1H), 6.84 (d, J=15.9 Hz, 1H), 7.07 (s, 2H), 7.37 (d, J=2.0 Hz, 1H), 7.60 (d, J=15.9 Hz, 1H), 7.83 (s, 2H), 7.93 (dd, J=8.0, 1.2 Hz, 1H), 8.07 (dd, J=6.9, 2.1 Hz, 1H), 8.18 (ddd, J=7.7, 6.2, 1.4 Hz, 1H), 8.48 (td, J=7.9, 1.4 Hz, 1H), 8.82 (d, J=6.9 Hz, 1H), 9.34 (dd, J=6.2, 1.3 Hz, 1H).

Example 22

(rac)-(E)-20-(2-(1,2,3,5,6,7-hexahydropyrido[3,2,1-ij]quinoline-9-yl)vinyl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate

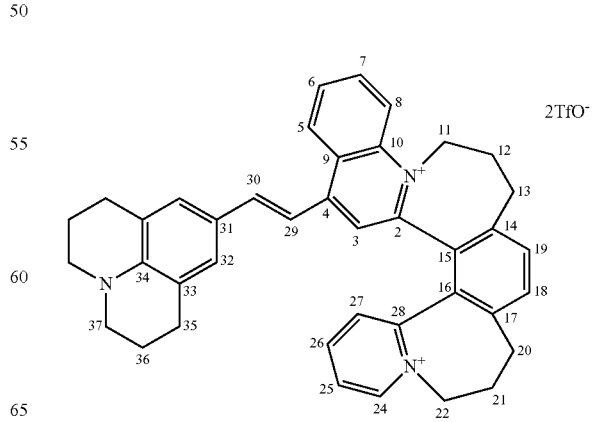

$^1$H NMR (600 MHz, acetonitrile-d$_3$): 1.90-1.95 (m, 4H, H-36), 2.32-2.39 (m, 1H, H-12a), 2.42-2.49 (m, 1H, H-13a), 2.48-2.55 (m, 1H, H-20a), 2.48-2.56 (m, 1H, H-21a), 2.65-2.73 (m, 1H, H-12b), 2.69-2.78 (m, 1H, H-21b), 2.73-2.76 (m, 4H, H-37), 2.98-3.05 (m, 1H, H-20b), 3.01-3.07 (m, 1H, H-13b), 3.33-3.36 (m, 4H, H-35), 4.36 (ddd, J=5.1, 13.4, 15.0 Hz, 1H, H-11a), 4.76 (dt, J=6.5; 13.3; 13.3 Hz, 1H, H-22a), 4.92 (bdd, J=6.3; 13.5 Hz, 1H, H-22b), 5.24 (bdd, J=5.6; 15.0 Hz, 1H, H-11b), 7.08 (d, J=15.2 Hz, 1H, H-29), 6.98 (s, 1H, H-3), 7.21 (s, 2H, H-32), 7.47 (bdd, J=0.6; 1.5; 8.0 Hz, 1H, H-27), 7.51 (dt, J=15.2, 0.5, 0.5 Hz, 1H, H-30), 7.72 (d, J=7.8 Hz, 1H, H-18), 7.74 (d, J=7.8 Hz, 1H, H-19), 7.86 (ddd, J=8.5, 6.9, 1.0 Hz, 1H, H-6), 7.93 (ddd, J=7.7, 6.2, 1.5 Hz, 1H, H-25), 8.13 (ddd, J=9.0, 6.9, 1.4 Hz, 1H, H-7), 8.15 (ddd, J=8.0, 7.7, 1.5 Hz, 1H, H-26), 8.34 (ddt, J=9.0, 1.0, 0.7, 0.7 Hz, 1H, H-8), 8.65 (ddt, J=8.5, 1.5, 0.7, 0.7 Hz, 1H, H-5), 8.96 (ddd, J=6.2, 1.5, 0.6 Hz, 1H, H-24).

Example 23

(rac)-(E)-13-(2-(6-(dimethylamino)naphthalene-2-yl)vinyl)-6,7-dimethyl-4,5,8,9-tetrahydroisoquinolino[1,2-a]pyrido[1,2-k][2,9]phenanthroline-3,10-diium trifluoromethanesulfonate

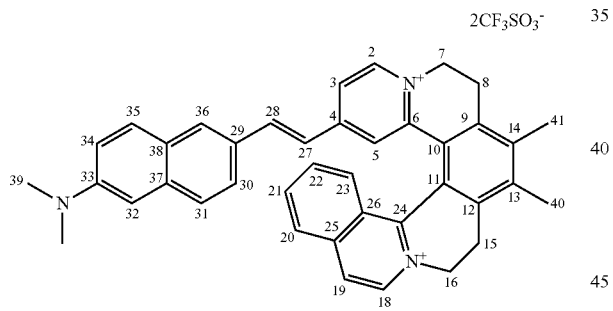

$^1$H NMR (600 MHz, acetone-d$_6$): 2.52 (s, 3H, H-40); 2.53 (s, 3H, H-41); 3.18 (s, 6H, H-39); 3.32 (bddd, J=5.2, 14.5, 17.0 Hz, 1H, H-15a); 3.44 (bdt, J=4.6, 16.0, 16.0 Hz, 1H, H-8a); 3.75 (ddd, J=1.9, 3.6, 17.0 Hz, 1H, H-8b); 3.75 (ddd, J=1.9, 3.8, 17.0 Hz, 1H, H-15b); 5.16 (dt, J=3.8, 14.0, 14.0 Hz, 1H, H-16a); 5.24 (ddd, J=1.9, 5.2, 13.6 Hz, 1H, H-16b); 5.26 (dt, J=3.6, 14.8, 14.8 Hz, 1H, H-7a); 5.41 (ddd, J=1.9, 4.6, 13.8 Hz, 1H, H-7b); 6.85 (d, J=16.0 Hz, 1H, H-27); 7.03 (d, J=2.6 Hz, 1H, H-32); 7.31 (dd, J=2.6, 9.0 Hz, 1H, H-34); 7.33 (d, J=16.0 Hz, 1H, H-28); 7.35 (d, J=2.0 Hz, 1H, H-5); 7.53 (dd, J=1.8, 8.6 Hz, 1H, H-30); 7.63 (d, J=8.6 Hz, 1H, H-31); 7.76 (ddd, J=1.2, 6.9, 8.7 Hz, 1H, H-22); 7.81 (bd, J=9.0 Hz, 1H, H-35); 7.86 (d, J=1.8 Hz, 1H, H-36); 7.86 (dd, J=2.0, 6.7 Hz, 1H, H-21); 7.94 (ddd, J=1.0, 6.9, 8.1 Hz, 1H, H-3); 8.08 (dq, J=0.9, 0.9, 0.9, 8.7 Hz, 1H, H-23); 8.17 (bddt, J=1.0, 6.9, 8.7 Hz, 1H, H-20); 8.55 (bd, J=6.8 Hz, 1H, H-19); 8.87 (d, J=6.7 Hz, 1H, H-2); 9.09 (d, J=6.8 Hz, 1H, H-18).

Example 24

(rac)-(E)-13-(2-(6-(dimethylamino)naphthalene-2-yl)vinyl)-4,5,8,9-tetrahydroiso-quinolino[2,1-k]pyrido[2,1-a][2,9]phenanthroline-3,10-diium trifluoromethanesulfonate

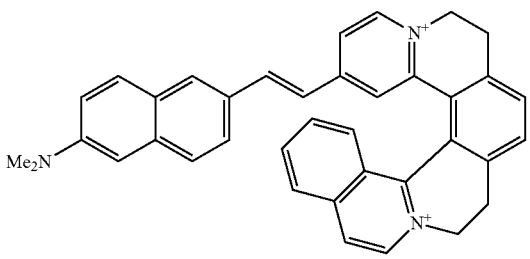

$^1$H NMR (400 MHz, acetone-d$_6$): 3.12 (s, 6H), 3.50-3.67 (m, 4H), 5.21-5.30 (m, 3H), 5.35-5.39 (m, 1H), 6.88 (d, J=16.2 Hz, 1H), 6.97 (d, J=2.4 Hz, 1H), 7.26 (dd, J=2.5; 9.1 Hz, 1H), 7.32 (d, J=16.2 Hz, 1H), 7.48 (d, J=1.7 Hz, 1H), 7.52 (dd, J=1.5; 8.8 Hz, 1H), 7.60 (d, J=8.7 Hz, 1H), 7.75 (dd, J=0.9; 8.8 Hz, 2H), 7.88 (s, 1H), 7.88 (dd, J=1.6; 6.6 Hz, 1H), 7.95 (t, J=7.4 Hz, 1H), 7.98 (dd, J=3.7; 7.8 Hz, 2H), 8.14 (d, J=8.7 Hz, 1H), 8.20 (d, J=8.2 Hz, 1H), 8.63 (d, J=6.7 Hz, 1H), 8.92 (d, J=6.6 Hz, 1H), 9.13 (d, J=6.7 Hz, 1H).

Example 25

(rac)-(E)-11-(2-(6-(dimethylamino)naphthalene-2-yl)vinyl)-6,7-dimethyl-4,5,8,9-tetrahydroisoquinolino[1,2-a]pyrido[1,2-k][2,9]phenanthroline-3,10-diium trifluoromethanesulfonate

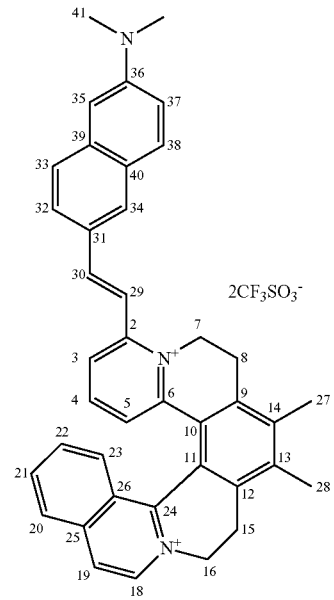 [SMILES: Cc1c(C)c2c(c3c1CC[n+]1ccc4ccccc4c1-3)-c1cccc(/C=C/c3ccc4cc(N(C)C)ccc4c3)[n+]1CC2]

¹H NMR (600 MHz, acetoned₆): 2.53 (s, 3H, H-27); 2.55 (s, 3H, H-28); 3.05 (bddd, J=4.8, 14.3, 17.3 Hz, 1H, H-8a); 3.11 (s, 6H, H-41); 3.16 (bddd, J=4.5, 15.1, 17.0 Hz, 1H, H-15a); 3.54 (ddd, J=1.8, 3.5, 17.0 Hz, 1H, H-15b); 3.58 (bdt, J=2.0, 3.8, 17.3 Hz, 1H, H-8b); 4.71 (dt, J=3.8, 14.0, 14.0 Hz, 1H, H-7a); 4.79 (dt, J=3.5, 14.5, 14.5 Hz, 1H, H-16a); 5.01 (ddd, J=1.8, 4.5, 13.8 Hz, 1H, H-16b); 5.38 (ddd, J=2.0, 4.8, 13.7 Hz, 1H, H-7b); 6.82 (dd, J=1.3, 8.0 Hz, 1H, H-3); 7.01 (bd, J=2.7 Hz, 1H, H-38); 7.28 (dd, J=2.7, 9.0 Hz, 1H, H-37); 7.49 (t, J=8.1 Hz, 1H, H-4); 7.58 (d, J=15.8 Hz, 1H, H-29); 7.65 (ddd, J=1.2, 6.9, 8.8 Hz, 1H, H-22); 7.74 (d, J=15.8 Hz, 1H, H-30); 7.77 (d, J=8.7 Hz, 1H, H-33); 7.80 (dq, J=1.0, 8.8 Hz, 1H, H-23); 7.82 (bd, J=9.0 Hz, 1H, H-35); 7.83 (dd, J=1.3, 8.2 Hz, 1H, H-5); 7.86 (dd, J=1.9, 8.7 Hz, 1H, H-32); 7.88 (ddd, J=1.1, 6.9, 8.1 Hz, 1H, H-21); 8.02 (bd, J=1.9 Hz, 1H, H-34); 8.12 (bdt, J=0.8, 0.8, 1.2, 8.1 Hz, 1H, H-20); 8.30 (bd, J=6.8 Hz, 1H, H-19); 8.60 (d, J=6.8 Hz, 1H, H-18).

Example 26

(E)-2-(2-(6-(dimethylamino) naphthalene-2-yl)vinyl)-6,7,10,11-tetrahydrodipyrido[2,1-a:1',2'-k][2,9]phenanthroline-5,12-diium trifluoromethanesulfonate

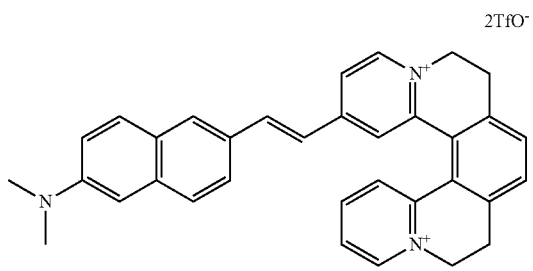 [SMILES: CN(C)c1ccc2cc(/C=C/c3cc[n+]4c(c3)-c3c(ccc5c3-c3cccc[n+]3CC5)CC4)ccc2c1]

¹H NMR (400 MHz, acetonitrile-d₃): 3.08 (s, 6H), 3.24-3.36 (m, 4H), 4.59-5.00 (m, 4H), 6.95 (d, J=2.5 Hz, 1H), 7.10 (d, J=16.2 Hz, 1H), 7.23 (dd, J=2.6, 9.1 Hz, 1H), 7.54-7.62 (m, 2H), 7.64 (d, J=7.6 Hz, 1H), 7.72 (s, 2H), 7.76 (d, J=9.2 Hz, 1H), 7.80-7.83 (m, 2H), 7.89-7.95 (m, 2H), 8.03-8.07 (m, 1H), 8.16-8.22 (m, 1H), 8.57 (d, J=6.7 Hz, 1H), 8.84-8.88 (m, 1H).

Example 27

(rac)-(E)-2-(2-(6-(dimethylamino) naphthalene-2-yl)vinyl)-6,7,8,11,12,13-hexahydrodipyrido[1,2-a:1',2'-a']benzo[2,1-c:3,4-c']bisazepinediium trifluoromethanesulfonate

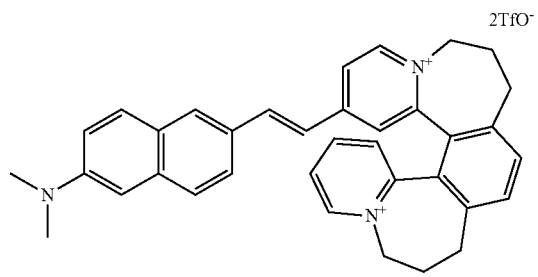 [SMILES: CN(C)c1ccc2cc(/C=C/c3cc[n+]4c(c3)-c3c(ccc5c3-c3cccc[n+]3CCC5)CCC4)ccc2c1]

¹H NMR (400 MHz, acetone-d₆): 2.42-2.95 (m, 6H), 3.06-3.17 (m, 2H), 3.11 (s, 6H), 4.71 (td, J=13.3, 5.8 Hz, 1H), 4.93 (tt, J=13.2, 5.6 Hz, 2H), 5.20 (dd, J=13.7, 6.3 Hz, 1H), 6.97 (d, J=2.4 Hz, 1H), 7.24 (dd, J=9.0, 2.5 Hz, 1H), 7.27 (d, J=16.1 Hz, 1H), 7.60 (d, J=2.1 Hz, 1H), 7.65 (s, 2H), 7.78 (d, J=9.1 Hz, 1H), 7.85 (s, 2H), 7.91 (d, J=16.1 Hz, 1H), 7.93 (d, J=7.5 Hz, 1H), 7.97 (s, 1H), 8.18 (ddd, J=7.6, 6.0, 1.3 Hz, 1H), 8.33 (dd, J=6.6, 2.1 Hz, 1H), 8.46 (td, J=7.9, 1.4 Hz, 1H), 9.05 (d, J=6.7 Hz, 1H), 9.35 (dd, J=6.2, 1.3 Hz, 1H).

Example 28

(rac)-4,15-bis((E)-2-(6-(dimethylamino) naphthalene-2-yl)vinyl)-6,7,8,11,12,13-hexahydrodipyrido[1,2-a:1',2'-a]benzo[2,1-c:3,4-c']bisazepinediium trifluoromethanesulfonate

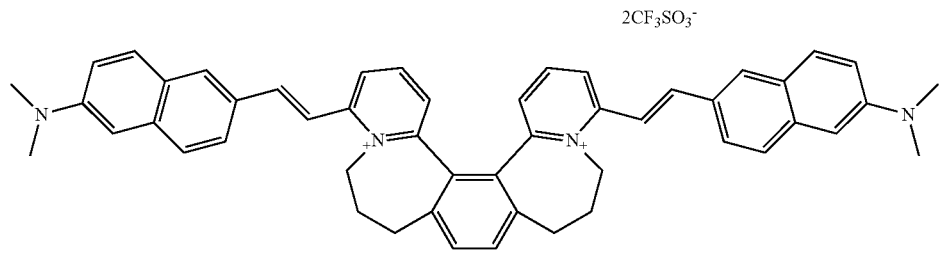

¹H NMR (600 MHz, acetonitriled₃): 2.40 (tt, J=5.8; 5.8; 13.5; 13.5 Hz, 2H), 2.48 (dt, J=6.9; 13.6; 14.4 Hz, 2H), 2.79 (tt, J=5.9; 5.9; 13.8; 13.8 Hz, 2H), 3.11 (s, 12H), 3.06 (dd, J=6.5; 14.4 Hz, 2H), 4.37 (ddd, J=5.0; 14.2; 14.5 Hz, 2H), 5.08 (dd, J=5.6; 14.5 Hz, 2H), 7.01 (d, J=2.6 Hz, 2H), 7.08 (dd, J=1.3; 7.7 Hz, 2H), 7.27 (dd, J=2.6; 9.1 Hz, 2H), 7.46 (d, J=15.7 Hz, 2H), 7.70 (s, 2H), 7.75 (d, J=8.7 Hz, 2H), 7.84 (d, J=9.1 Hz, 2H), 7.89 (dd, J=1.9; 8.7 Hz, 2H), 7.91 (d, J=15.7 Hz, 2H), 8.03 (t, J=8.1 Hz, 2H), 8.09 (d, J=1.9 Hz, 2H), 8.26 (dd, J=1.3; 8.4 Hz, 2H).

Example 29

(rac)-(E)-20-(2-(6-(dimethylamino) naphthalene-2-yl)vinyl)-6,7,8,11,12,13-hexahydropyrido[1''',2''':1'',2'']azepino[4'',3'':5',6']benzo[1',2',3,4]azepino[1,2-a]quinoline-5,14-diium trifluoromethanesulfonate

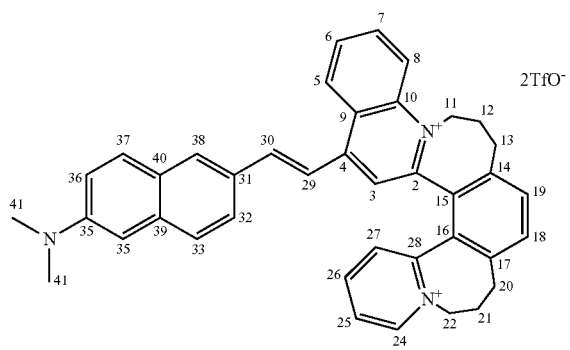

$^1$H NMR (600 MHz, acetonitrile-$d_3$): 2.42-2.57 (m, 4H, H-21a, H-20a, H-13a a H-12a), 2.72-2.80 (m, 2H, H-21b a H-12b), 3.10 (s, 6I-1, H-41), 3.02-3.11 (m, 2H, H-20b a H-13b), 4.52 (ddd, J=15.0, 13.3, 5.2 Hz, 1H, H-11a), 4.80 (dt, J=12.8, 12.8, 5.9 Hz, 1H, H-22a), 4.95 (bdd, J=13.7, 6.5 Hz, 1H, H-22b), 5.41 (bdd, J=15.0, 5.5 Hz, 1H, H-11b), 6.98 (d, J=2.7 Hz, 1H, H-34), 7.25 (bd, J=15.6 Hz, 1H, H-30), 7.26 (dd, J=9.1, 2.7 Hz, 1H, H-36), 7.27 (bs, 1H, H-3), 7.46 (bdd, J=8.1, 1.4 Hz, 1H, H-27), 7.71 (d, J=8.7 Hz, 1H, H-33), 7.77 (d, J=7.9 Hz, 1H, H-18), 7.79 (d, J=7.9 Hz, 1H, H-19), 7.81 (dd, J=8.7, 1.9 Hz, 1H, H-32), 7.83 (bdq, J=9.1, 3×0.5 Hz, 1H, H-37), 7.90 (bd, J=15.6 Hz, 1H, H-29), 7.94 (bd, J=1.9 Hz, 1H, H-38), 7.98 (ddd, J=7.7, 6.2, 1.4 Hz, 1H, H-25), 8.00 (ddd, J=8.5, 6.9, 1.0 Hz, 1H, H-6), 8.17 (dt, J=7.9, 7.9, 1.5 Hz, 1H, H-26), 8.26 (ddd, J=9.0, 6.9, 1.4 Hz, 1H, H-7), 8.51 (bdq, J=9.0, 3×0.8 Hz, 1H, H-8), 8.76 (ddt, J=8.5, 1.5, 0.6, 0.6 Hz, 1H, H-5), 9.01 (ddd, J=6.2, 1.5, 0.6 Hz, 1H, H-24).

Example 30

(rac)-(E)-2-(2-(4-(dimethylamino) naphthalene-1-yl)vinyl)-6,7,8,11,12,13-hexahydrodipyrido[1,2-a:1',2'-a']benzo[2,1-c:3,4-c']bisazepinediium trifluoromethanesulfonate

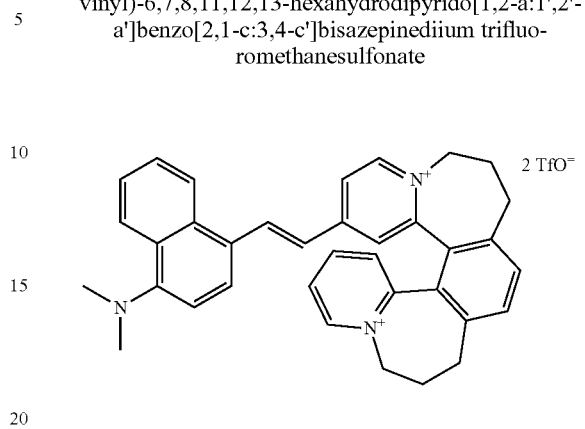

$^1$H NMR (400 MHz, acetone-$d_6$): 2.43-2.92 (m, 6H), 2.96 (s, 6H), 3.08-3.21 (m, 2H), 4.73 (td, J=13.2, 5.7 Hz, 1H), 4.87-5.05 (m, 2H), 5.18 (dd, J=13.7, 6.3 Hz, 1H), 7.13 (dd, J=8.1, 0.3 Hz, 1H), 7.28 (dd, J=16.0, 0.4 Hz, 1H), 7.53-7.63 (m, 2H), 7.70 (d, J=1.8 Hz, 1H), 7.86 (s, 2H), 7.94-7.99 (m, 2H), 8.18 (ddd, J=7.7, 6.1, 1.5 Hz, 1H), 8.23-8.27 (m, 1H), 8.34-8.39 (m, 1H), 8.48 (td, J=7.9, 1.5 Hz, 1H), 8.56 (ddd, J=6.6, 2.1, 0.3 Hz, 1H), 8.64 (d, J=15.9 Hz, 1H), 9.10 (d, J=6.8 Hz, 1H), 9.34 (ddd, J=6.1, 1.4, 0.4 Hz, 1H).

Example 31

(rac)-4,15-bis((E)-2-(4-(dimethylamino) naphthalene-1-yl)vinyl)-6,7,8,11,12,13-hexahydrodipyrido[1,2-a:1',2'-a']benzo[2,1-c:3,4-c']bisazepinediium trifluoromethanesulfonate

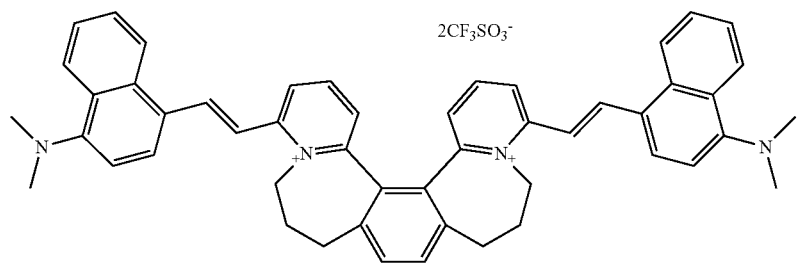

$^1$H NMR (600 MHz, acetonitrile-$d_3$): 2.38 (tt, J=5.8; 5.8; 13.5; 13.5 Hz, 2H), 2.50 (ddd, J=7.0; 13.6; 14.1 Hz, 2H), 2.78 (tt, J=6.1; 6.1; 13.5; 13.5 Hz, 2H), 3.00 (s, 12H), 3.07 (ddd, J=0.9; 6.5; 14.1 Hz, 2H), 4.39 (ddd, J=4.4; 13.4; 14.6 Hz, 2H), 5.10 (dd, J=5.8; 14.6 Hz, 2H), 7.16 (dd, J=1.3; 7.8 Hz, 2H), 7.22 (d, J=8.0 Hz, 2H), 7.51 (d, J=15.4 Hz, 2H), 7.62 (ddd, J=1.3; 6.7; 8.4 Hz, 2H), 7.68 (ddd, J=1.4; 6.7; 8.4 Hz, 2H), 7.71 (s, 2H), 8.11 (ddd, J=6.6; 7.8; 8.4 Hz, 2H), 8.14 (dd, J=0.6; 8.0 Hz, 2H), 8.30 (ddd, J=0.6; 1.3; 8.4 Hz, 2H), 8.38 (dd, J=0.6; 1.4; 8.4 Hz, 2H), 8.38 (dd, J=1.3; 8.4 Hz, 2H), 8.54 (bd, J=7.0; 15.4 Hz, 2H).

Example 32

(rac)-13-((1E,3E)-4-(4-(dimethylamino)phenyl)buta-1,3-dienyl)-6,7-dimethyl-4,5,8,9-tetrahydroisoquinolino[1,2-a]pyrido[1,2-k][2,9]phenanthroline-3,10-diium trifluoromethanesulfonate

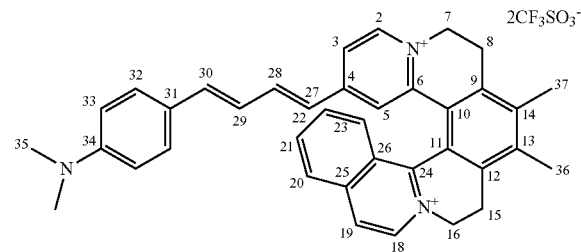

¹H NMR (600 MHz, acetone-d₆): 2.52 (s, 3H); 2.52 (s, 3H); 2.99 (s, 6H); 3.10-3.18 (m, 1H); 3.23 (bdt, J=4.3, 16.0, 16.0 Hz, 1H); 3.56-3.62 (m, 2H); 4.92 (dt, J=3.7, 14.3, 14.3 Hz, 1H); 4.94-5.00 (m, 1H); 5.20 (ddd, J=1.8, 4.3, 14.2 Hz, 1H); 6.05 (d, J=15.3 Hz, 1H); 6.70-6.73 (m, 2H); 6.72 (dd, J=10.5, 15.3 Hz, 1H); 6.80 (d, J=15.3 Hz, 1H); 6.92 (dd, J=10.5, 15.3 Hz, 1H); 7.07 (d, J=2.0 Hz, 1H); 7.42-7.45 (m, 2H); 7.62 (ddd, J=1.2, 6.9, 8.7 Hz, 1H); 7.63 (dd, J=2.0, 6.7 Hz, 1H); 7.89 (dq, J=0.9, 0.9, 0.9, 8.7 Hz, 1H); 7.92 (ddd, J=1.2, 6.9, 8.7 Hz, 1H); 8.16 (bd, J=8.2 Hz, 1H); 8.55 (bd, J=6.7 Hz, 1H); 8.77 (d, J=6.7 Hz, 1H); 9.07 (d, J=6.7 Hz, 1H).

Example 33

(rac)-11-((1E,3E)-4-(4-(dimethylamino)phenyl)buta-1,3-dienyl)-6,7-dimethyl-4,5,8,9-tetrahydroisoquinolino[1,2-a]pyrido[1,2-k][2,9]phenanthroline-3,10-diium trifluoromethanesulfonate

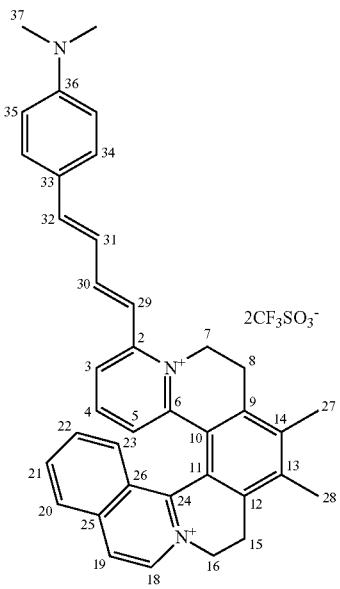 [SMILES: Cc1c(C)c2c(c3c1CC[n+]1ccc4ccccc4c1-3)-c1cccc(/C=C/C=C/c3ccc(N(C)C)cc3)[n+]1CC2]

¹H NMR (600 MHz, acetone-d₆): 2.66 (s, 3H, H-27); 2.67 (s, 3H, H-28); 3.10 (s, 6H, H-37); 3.35 (bddd, J=4.8, 14.8, 17.4 Hz, 1H, H-8a); 3.49 (ddd, J=4.5, 14.8, 17.2 Hz, 1H, H-15a); 3.82 (ddd, J=1.8, 3.7, 17.2 Hz, 1H, H-15b); 3.86 (ddd, J=2.0, 3.7, 17.4 Hz, 1H, H-8b); 5.07 (dt, J=3.7, 14.5, 14.5 Hz, 1H, H-7a); 5.18 (bdt, J=3.7, 14.4, 14.4 Hz, 1H, H-16a); 5.40 (ddd, J=1.8, 4.5, 14.0 Hz, 1H, H-16b); 5.60 (ddd, J=2.0, 4.8, 13.7 Hz, 1H, H-7b); 6.81-6.84 (m, 2H, H-35); 7.16 (d, J=15.3 Hz, 1H, H-32); 7.21 (dd, J=10.0, 15.3 Hz, 1H, H-31); 7.30 (dd, J=1.3, 8.0 Hz, 1H, H-5); 7.34 (d, J=14.9 Hz, 1H, H-29); 7.52-7.55 (m, 2H, H-34); 7.64 (t, J=8.1 Hz, 1H, H-4); 7.75 (dd, J=10.0, 14.9 Hz, 1H, H-30); 7.81 (ddd, J=1.2, 6.9, 8.8 Hz, 1H, H-22); 8.01 (ddd, J=1.1, 6.9, 8.1 Hz, 1H, H-21); 8.04 (dd, J=1.3, 8.2 Hz, 1H, H-3); 8.14 (dq, J=0.9, 0.9, 0.9, 8.8 Hz, 1H, H-23); 8.29 (bd, J=8.1 Hz, 1H, H-20); 8.55 (bd, J=6.7 Hz, 1H, H-19); 9.03 (d, J=6.7 Hz, 1H, H-18).

Example 34

2-((1E,3E)-4-(4-(dimethylamino)phenyl)buta-1,3-dien-1-yl)-6,7,10,11-tetrahydrodipyrido[2,1-a:1',2'-k][2,9]phenanthroline-5,12-diium trifluoromethanesulfonate, i.e. 30

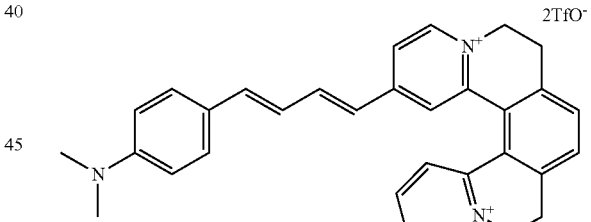

¹H NMR (400 MHz, acetonitrile-d₃): 3.00 (s, 6H), 3.19-3.38 (m, 4H), 4.52-4.98 (m, 4H), 6.41 (d, J=15.3 Hz, 1H), 6.70-6.75 (m, 2H), 6.80-6.95 (m, 2H), 7.32 (dd, J=10.3, 15.3 Hz, 1H), 7.40-7.45 (m, 2H), 7.62 (d, J=1.9 Hz, 1H), 7.71 (s, 2H), 7.76 (dd, J=2.0, 6.7 Hz, 1H), 7.88-7.93 (m, 1H), 8.00-8.04 (m, 1H), 8.18 (td, J=8.1, 1.4 Hz, 1H), 8.46 (d, J=6.7 Hz, 1H), 8.81-8.85 (m, 1H).

Example 35

(rac)-11-((1E,3E)-4-(1,2,3,5,6,7-hexahydropyrido[3,2,1-ij]quinoline-9-yl)buta-1,3-dienyl)-6,7-dimethyl-4,5,8,9-tetrahydroisoquinolino[1,2-a]pyrido[1,2-k][2,9]phenanthroline-3,10-diium trifluoromethanesulfonate

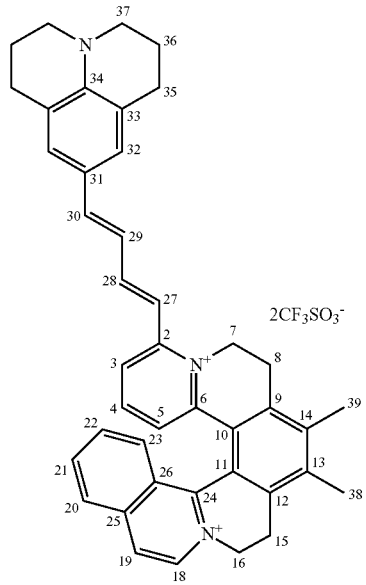 [SMILES: Cc1c(C)c2c(c3c1CC[n+]1ccc4ccccc4c1-3)-c1cccc(/C=C/C=C/c3cc4c5c(c3)CCCN5CCC4)[n+]1CC2]

$^1$H NMR (600 MHz, acetone$_6$): 1.96-2.01 (m, 4H, H-36); 2.65 (s, 3H, H-38); 2.66 (s, 3H, H-39); 2.77 (bt, J=6.4 Hz, 4H, H-35); 3.32-3.35 (m, 4H, H-37); 3.33 (ddd, J=4.8, 14.5, 17.2 Hz, 1H, H-8a); 3.47 (bddd, J=4.6, 14.2, 17.0 Hz, 1H, H-15a); 3.80 (ddd, J=1.8, 3.5, 17.0 Hz, 1H, H-15b); 3.84 (ddd, J=1.9, 3.5, 17.2 Hz, 1H, H-8b); 5.04 (bdt, J=3.5, 14.2, 14.2 Hz, 1H, H-7a); 5.16 (bdt, J=3.5, 14.0, 14.0 Hz, 1H, H-16a); 5.39 (ddd, J=1.8, 4.6, 13.8 Hz, 1H, H-16b); 5.55 (bddd, J=1.9, 4.8, 13.9 Hz, 1H, H-7b); 7.05 (bd, J=15.1 Hz, 1H, H-30); 7.08 (bd, J=0.6 Hz, 2H, H-32); 7.14 (ddd, J=0.7, 10.7, 15.1 Hz, 1H, H-29); 7.26 (dd, J=1.3, 7.9 Hz, 1H, H-5); 7.26 (bd, J=14.8 Hz, 1H, H-27); 7.59 (t, J=8.1 Hz, 1H, H-4); 7.74 (dd, J=10.7, 14.8 Hz, 1H, H-28); 7.80 (ddd, J=1.3, 7.0, 8.8 Hz, 1H, H-22); 8.00 (ddd, J=1.1, 7.0, 8.1 Hz, 1H, H-21); 8.01 (dd, J=1.3, 8.4 Hz, 1H, H-3); 8.29 (ddt, J=0.7, 0.7, 1.3, 8.1 Hz, 1H, H-20); 8.29 (dq, J=0.9, 0.9, 0.9, 8.8 Hz, 1H, H-23); 8.54 (dd, J=0.9, 6.7 Hz, 1H, H-19); 9.03 (d, J 6.7 Hz, 1H, H-18).

Example 36

(M)-(E)-13-(4-methoxystyryl)-6,7-dimethyl-4,5,8,9-tetrahydroisoquinolino[1,2-a]pyrido[1,2-k][2,9]phenanthroline-3,10-diium trifluoromethanesulfonate, i.e. (M)-6

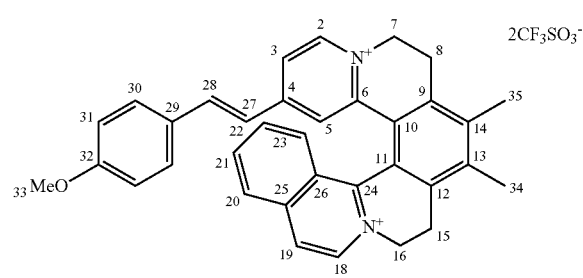

$^1$H NMR (600 MHz, acetoned$_6$): 2.64 (s, 3H, H-34); 2.65 (s, 3H, H-35); 3.39 (bddd, J=5.2, 14.5, 17.0 Hz, 1H, H-15a); 3.47 (bdt, J=4.6, 15.8, 15.8 Hz, 1H, H-8a); 3.81 (ddd, J=1.9, 3.6, 17.0 Hz, 1H, H-15b); 3.81 (ddd, J=1.9, 3.7, 17.0 Hz, 1H, H-8b); 3.89 (s, 3H, H-33); 5.21 (dt, J=3.7, 14.5, 14.5 Hz, 1H, H-7a); 5.24 (dt, J=3.6, 14.0, 14.0 Hz, 1H, H-16a); 5.27 (ddd, J=1.9, 5.2, 13.7 Hz, 1H, H-16b); 5.38 (ddd, J=1.9, 4.6, 14.1 Hz, 1H, H-7b); 6.80 (d, J=16.3 Hz, 1H, H-27); 6.96-6.98 (m, 2H, H-31); 7.28 (d, J=16.3 Hz, 1H, H-28); 7.40 (d, J=2.0 Hz, 1H, H-5); 7.55-7.57 (m, 21-1, H-30); 7.79 (ddd, J=1.3, 6.9, 8.7 Hz, 1H, H-22); 7.89 (dd, J=2.0, 6.6 Hz, 1H, H-3); 7.96 (ddd, J=1.1, 6.9, 8.1 Hz, 1H, H-21); 8.13 (dq, J=0.9, 0.9, 0.9, 8.7 Hz, 1H, H-23); 8.21 (bdt, J=0.7, 0.7, 1.3, 8.1 Hz, 1H, H-20); 8.57 (bd, J=6.7 Hz, 1H, H-19); 8.92 (d, J=6.6 Hz, 1H, H-2); 9.08 (d, J=6.7 Hz, 1H, H-18).

Example 37

(rac)-(E)-13-(4-methoxystyryl)-4,5,8,9-tetrahydroisoquinolino[2,1-k]pyrido[2,1-a][2,9]phenanthroline-3,10-diium trifluoromethanesulfonate

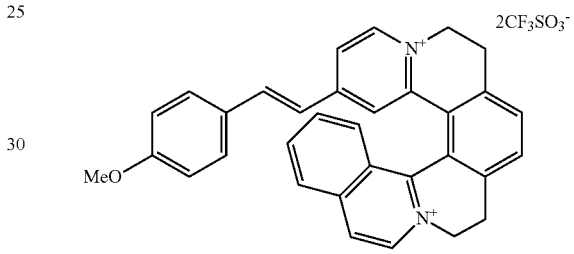

$^1$H NMR (400 MHz, acetone-d$_6$): 3.53-3.62 (m, 4H), 3.84 (s, 3H), 5.19-5.35 (m, 4H), 6.78 (d, J=16.0 Hz, 1H), 6.93 (d, J=8.4 Hz, 2H), 7.25 (d, J=16.0 Hz, 1H), 7.51 (s, 2H), 7.53 (d, J=7.2 Hz, 1H), 7.75 (t, J=7.6 Hz, 1H), 7.88 (d, J=6.0 Hz, 1H), 7.94 (t, J=7.6 Hz, 1H), 8.01 (dd, J=3.6; 8.0 Hz, 2H), 8.11 (d, J=8.8 Hz, 1H), 8.19 (d, J=8.4 Hz, 1H), 8.59 (d, J=6.4 Hz, 1H), 8.93 (d, J=6.4 Hz, 1H), 9.08 (d, J=6.8 Hz, 1H).

Example 38

(rac)-(E)-19-(4-methoxystyryl)-8,9,10,13,14,15-hexahydropyrido[1',2''':1'',2'']azepino[4'',3'':5',6']benzo[1',2',3,4]azepino[2,1-a]isoquinoline-7,16-diium trifluoromethanesulfonate

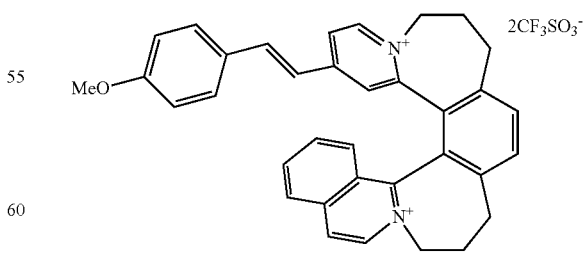

$^1$H NMR (400 MHz, acetone-d$_6$): 2.51-2.66 (m, 3H), 2.71-2.78 (m, 3H), 3.17-3.24 (m, 2H), 3.85 (s, 3H), 4.85 (dt, J=5.2;

13.2 Hz, 1H), 5.07 (m, 2H), 5.30 (dd, J=5.6; 14.0 Hz, 1H), 6.96 (d, J=8.8 Hz, 2H), 6.97 (d, J=16.2 Hz, 1H), 7.19 (d, J=1.2 Hz, 1H), 7.58 (d, J=16.4 Hz, 1H), 7.61 (d, J=8.8 Hz, 2H), 7.92 (t, J=8.0 Hz, 1H), 7.99-8.03 (m, 4H), 8.08 (t, J=7.2 Hz, 1H), 8.29 (d, J=8.0 Hz, 1H), 8.68 (d, J=6.4 Hz, 1H), 8.88 (d, J=6.4 Hz, 1H), 9.16 (d, J=6.8 Hz, 1H).

Example 39

(rac)-(E)-11-(4-methoxystyryl)-6,7-dimethyl-4,5,8,9-tetrahydroisoquinolino[1,2-a]pyrido[1,2-k][2,9]phenanthroline-3,10-diium trifluoromethanesulfonate

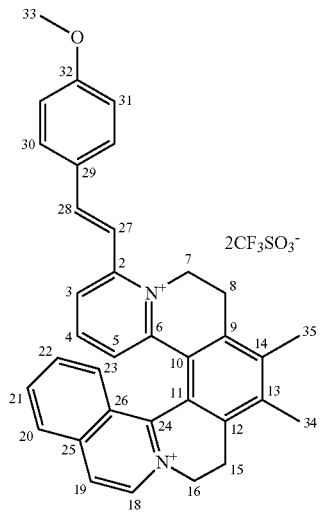 [SMILES: COc1ccc(/C=C/c2cccc3[n+]2CCc2c(C)c(C)c4c(c2-3)-c2c3ccccc3cc[n+]2CC4)cc1]

$^1$H NMR (600 MHz, acetone-d$_6$): 2.66 (bs, 3H, H-34); 2.66 (bs, 3H, H-35); 3.38 (bddd, J=4.7, 14.6, 16.8 Hz, 1H, H-8a); 3.50 (ddd, J=4.6, 14.3, 16.8 Hz, 1H, H-15a); 3.84 (ddd, J=1.9, 3.6, 16.8 Hz, 1H, H-8b); 3.84 (ddd, J=1.9, 3.6, 16.8 Hz, 1H, H-15b); 3.94 (s, 3H, H-33); 5.18 (dt, J=3.6, 14.3, 14.4 Hz, 1H, H-7a); 5.20 (dt, J=3.6, 14.2, 14.2 Hz, 1H, H-16a); 5.41 (ddd, J=1.9, 4.6, 14.1 Hz, 1H, H-16b); 5.74 (ddd, J=1.9, 4.7, 13.7 Hz, 1H, H-7b); 7.11-7.17 (m, 2H, H-31); 7.44 (dd, J=1.3, 8.0 Hz, 1H, H-5); 7.75 (t, J=8.1 Hz, 1H, H-4); 7.83 (d, J=15.9 Hz, 1H, H-28); 7.85 (ddd, J=1.2, 6.9, 8.7 Hz, 1H, H-22); 7.88-7.91 (m, 2H, H-31); 7.90 (d, J=15.9 Hz, 1H, H-27); 8.00 (ddd, J=1.1, 6.9, 8.1 Hz, 1H, H-21); 8.11 (dd, J=1.3, 8.2 Hz, 1H, H-3); 8.14 (dq, J=0.9, 0.9, 0.9, 8.7 Hz, 1H, H-23); 8.30 (bddt, J=0.7, 0.7, 1.2, 8.1 Hz, 1H, H-20); 8.57 (bd, J=6.7 Hz, 1H, H-19); 9.05 (d, J=6.7 Hz, 1H, H-18).

Example 40

(E)-2-(4-methoxystyryl)-6,7,10,11-tetrahydrodipyrido[2,1-a:1',2'-k][2,9]phenanthroline-5,12-diium trifluoromethanesulfonate

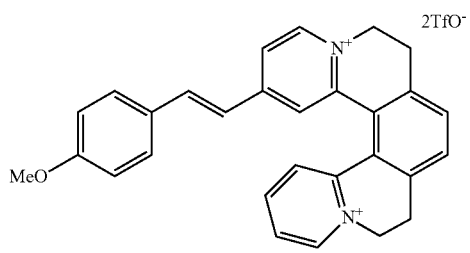 [SMILES: COc1ccc(/C=C/c2cc[n+]3c(c2)-c2c(ccc4c2-c2cccc[n+]2CC4)CC3)cc1]

$^1$H NMR (400 MHz, acetonitrile-d$_3$): 3.19-3.40 (m, 4H), 3.83 (s, 3H), 4.59-4.99 (m, 4H), 6.95-7.03 (m, 3H), 7.44 (d, J=16.3 Hz, 1H), 7.51-7.57 (m, 2H), 7.72 (s, 2H), 7.78 (d, J=1.9 Hz, 1H), 7.88-7.93 (m, 2H), 8.00-8.04 (m, 1H), 8.18 (dt, J=1.4, 8.2 Hz, 1H), 8.58 (d, J=6.7 Hz, 1H), 8.83 (d, J=6.1 Hz, 1H).

Example 41

(rac)-(E)-20-(4-methoxystyryl)-6,7,8,11,12,13-hexahydropyrido[1''',2''':1'',2'']azepino[4'',3'':5',6']benzo[1',2':3,4]azepino[1,2-a]quinoline-5,14-diium trifluoromethanesulfonate

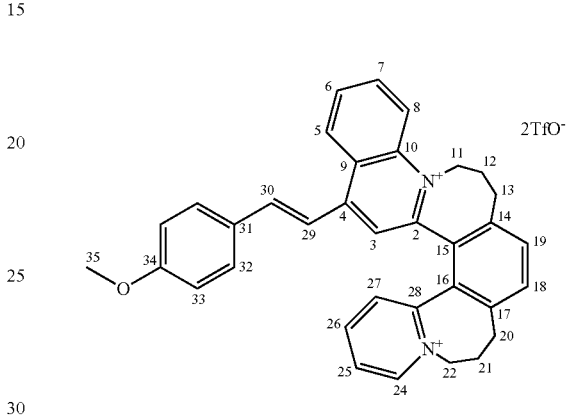

$^1$H NMR (600 MHz, acetonitrile-d$_3$): 2.46-2.51 (m, 1H, H-12a), 2.46-2.53 (m, 2H, H-20a and H-13a), 2.53-2.60 (m, 1H, H-21a), 2.74-2.80 (m, 1H, H-21b), 2.77-2.82 (m, 1H, H-12b), 3.04-3.11 (m, 2H, H-20b and H-13b), 3.91 (s, 3H, H-35), 4.57 (ddd, J=14.8, 13.3, 4.3 Hz, 1H, H-11a), 4.80 (dt, J=13.2, 13.2, 5.5 Hz, 1H, H-22a), 4.94 (dd, J=13.6, 6.2 Hz, 1H, H-22b), 5.47 (dd, J=14.8, 5.9 Hz, 1H, H-11b), 7.06-7.09 (m, 2H, H-33), 7.15 (d, J=15.8 Hz, 1H, H-30), 7.27 (s, 1H, H-3), 7.48 (dd, J=8.1, 1.5 Hz, 1H, H-27), 7.72-7.75 (m, 2H, H-32), 7.80 (d, J=7.8 Hz, 1H, H-18), 7.81 (d, J=15.8 Hz, 1H, H-29), 7.82 (d, J=7.8 Hz, 1H, H-19), 8.01 (ddd, J=7.7, 6.1, 1.5 Hz, 1H, H-25), 8.04 (ddd, J=8.6, 6.9, 1.0 Hz, 1H, H-6), 8.19 (dt, J=7.9, 7.9, 1.5 Hz, 1H, H-26), 8.30 (ddd, J=9.0, 6.9, 1.4 Hz, 1H, H-7), 8.56 (bd, J=9.0 Hz, 1H, H-8), 8.76 (dd, J=8.5, 1.5 Hz, 1H, H-5), 9.01 (bdd, J=6.1, 1.5 Hz, 1H, H-24).

Example 42

(rac)-(E)-13-(2-(6-methoxynaphthalene-2-yl)vinyl)-4,5,8,9-tetrahydroisoquinolino-[2,1-k]pyrido[2,1-a][2,9]phenanthroline-3,10-diium trifluoromethanesulfonate

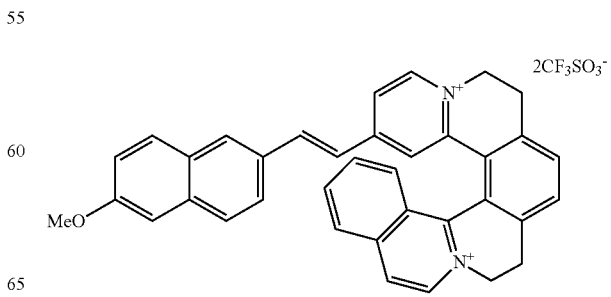

$^1$H NMR (400 MHz, acetone-d$_6$): 3.58-3.67 (m, 4H), 3.94 (s, 3H), 5.23-5.32 (m, 3H), 5.35-5.41 (m, 1H), 7.03 (d, J=16.2 Hz, 1H), 7.19 (dd, J=2.5; 8.9 Hz, 1H), 7.33 (d, J=2.4 Hz, 1H), 7.40 (d, J=16.2 Hz, 1H), 7.59 (d, J=1.5 Hz, 1H), 7.66 (dd, J=1.5; 8.5 Hz, 1H), 7.76 (dt, J=0; 7.5 Hz, 1H), 7.78 (d, J=8.7 Hz, 1H), 7.85 (d, J=8.7 Hz, 1H), 7.96 (m, 3H), 8.02 (dd, J=5.7; 7.7 Hz, 2H), 8.17 (d, J=8.7 Hz, 1H), 8.22 (d, J=8.2 Hz, 1H), 8.64 (d, J=6.6 Hz, 1H), 9.01 (d, J=6.4 Hz, 1H), 9.13 (d, J=6.6 Hz, 1H).

Example 43

(rac)-(E)-11-(2-(6-methoxynaphthalene-2-yl)vinyl)-6,7-dimethyl-4,5,8,9-tetrahydroisoquinolino[1,2-a]pyrido[1,2-k][2,9]phenanthroline-3,10-thium trifluoromethanesulfonate

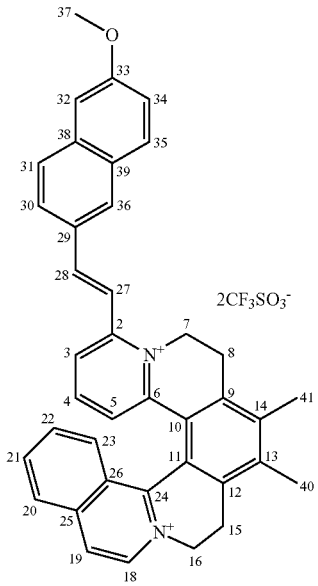 [SMILES: COc1ccc2cc(/C=C/c3cccc4[n+]3CCc3c(C)c(C)c5c(c3-4)-c3c4ccccc4cc[n+]3CC5)ccc2c1]

$^1$H NMR (600 MHz, acetonitrile-d$_3$): 2.54 (s, 3H, H-40); 2.55 (s, 3H, H-41); 3.07 (ddd, J=4.9, 14.8, 17.2 Hz, 1H, H-8a); 3.18 (ddd, J=4.5, 14.8, 17.2 Hz, 1H, H-15a); 3.56 (ddd, J=1.8, 3.6, 17.2 Hz, 1H, H-15b); 3.60 (ddd, J=1.8, 3.8, 17.2 Hz, 1H, H-8b); 3.96 (s, 3H); 4.77 (dt, J=3.8, 14.4, 14.4 Hz, 1H, H-7a); 4.84 (ddd, J=3.6, 14.3, 14.3 Hz, 1H, H-16a); 5.04 (ddd, J=1.8, 4.5, 13.8 Hz, 1H, H-16b); 5.41 (ddd, J=1.8, 4.9, 14.0 Hz, 1H, H-7b); 6.92 (dd, J=1.1, 8.0 Hz, 1H, H-5); 7.24 (dd, J=2.6, 8.8 Hz, 1H, H-34); 7.35 (d, J=2.6 Hz, 1H, H-32); 7.55 (t, J=8.1 Hz, 1H, H-4); 7.68 (ddd, J=1.2, 6.9, 8.7 Hz, 1H, H-22); 7.69 (d, J=15.9 Hz, 1H, H-27); 7.74 (d, J=15.9 Hz, 1H, H-28); 7.82 (dq, J=1.0, 1.0, 1.0, 8.7 Hz, 1H, H-23); 7.84 (dd, J=1.1, 8.2 Hz, 1H, H-3); 7.88 (ddd, J=1.1, 6.9, 8.1 Hz, 1H, H-21); 7.90 (d, J=8.8 Hz, 1H, H-35); 7.92 (d, J 8.6 Hz, 1H, H-31); 7.95 (dd, J=1.8, 8.6 Hz, 1H, H-30); 8.12 (bd, J=8.1 Hz, 1H, H-20); 8.16 (d, J=1.8 Hz, 1H, H-36); 8.30 (bd, J=6.7 Hz, 1H, H-19); 8.62 (d, J=6.7 Hz, 1H, H-18).

Example 44

(E)-2-(2-(6-methoxynaphthalene-2-yl)vinyl)-6,7,10,11-tetrahydrodipyrido[2,1-a:1',2'-k][2,9]phenanthroline-5,12-diium trifluoromethanesulfonate

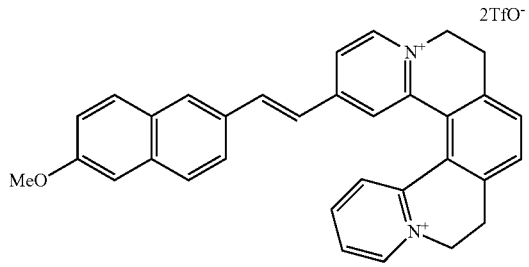 [SMILES: COc1ccc2cc(/C=C/c3cc[n+]4c(c3)-c3c(ccc5c3-c3cccc[n+]3CC5)CC4)ccc2c1]

$^1$H NMR (400 MHz, acetonitrile-d$_3$): 3.21-3.41 (m, 4H), 3.92 (s, 3H), 4.62-5.01 (m, 4H), 7.17-7.24 (m, 2H), 7.30 (d, J=2.4 Hz, 1H), 7.60 (d, J=16.3 Hz, 1H), 7.71 (dd, J=1.7, 8.7 Hz, 1H), 7.73 (s, 2H), 7.80-7.87 (m, 3H), 7.90-7.95 (m, 2H), 7.98 (dd, J=1.9, 6.7 Hz, 1H), 8.04 (d, J=7.5 Hz, 1H), 8.16-8.22 (m, 1H), 8.62 (d, J=6.7 Hz, 1H), 8.86 (d, J=5.5 Hz, 1H).

Example 45

(rac)-4,15-bis((E)-2-(6-methoxynaphthalene-2-yl)vinyl)-6,7,8,11,12,13-hexahydrodipyrido[1,2-a:1',2'-a']benzo[2,1-c:3,4-c']bisazepinediium trifluoromethanesulfonate

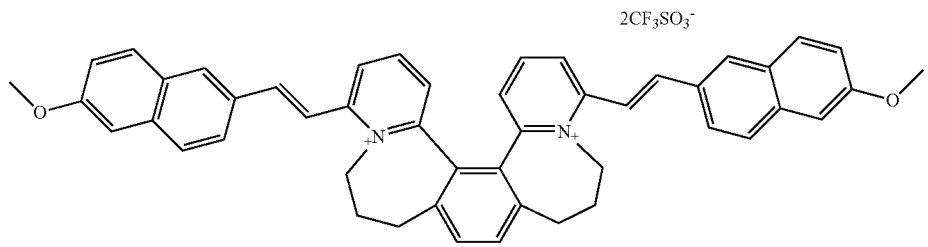

$^1$H NMR (600 MHz, acetonitrile d$_3$): 2.42 (tt, J=5.4; 5.4; 13.5; 13.5 Hz, 2H), 2.48 (dt, J=7.0; 13.5; 13.5 Hz, 2H), 2.81 (tt, J=6.0; 6.0; 13.7; 13.7 Hz, 2H), 3.07 (dd, J=5.9; 13.4 Hz, 2H), 3.95 (s, 6H), 4.40 (ddd, J=5.1; 13.5; 14.6 Hz, 2H), 5.10 (dd, J=5.8; 14.6 Hz, 2H), 7.15 (dd, J=1.3; 7.8 Hz, 2H), 7.26 (dd, J=2.5; 8.8 Hz, 2H), 7.36 (d, J=2.5 Hz, 2H), 7.56 (d, J=15.8 Hz, 2H), 7.72 (s, 2H), 7.92 (bd, J=8.5 Hz, 2H), 7.92 (dd, J=1.0; 8.8 Hz, 2H), 7.92 (d, J=15.8 Hz, 2H), 8.00 (dd, J=1.8; 8.5 Hz, 2H), 8.09 (t, J=8.1 Hz, 2H), 8.22 (bdt, J=1.0; 1.0; 1.8 Hz, 2H), 8.28 (dd, J=1.3; 8.3 Hz, 2H).

Example 46

(rac)-(E)-20-(2-(6-methoxynaphthalene-2-yl)vinyl)-6,7,8,11,12,13-hexahydropyrido[1''',2''':1'',2'']azepino[4'',3'':5',6']benzo[1',2'3,4]azepino[1,2-a]quinoline-5,14-diium trifluoromethanesulfonate

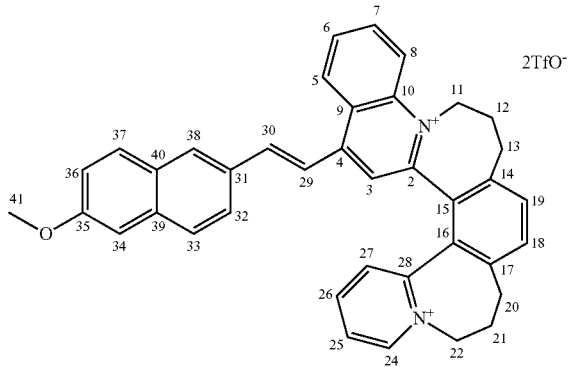 [SMILES: COc1ccc2cc(/C=C/c3cc4[n+](c5ccccc35)CCCc3ccc5c(c3-4)-c3cccc[n+]3CCC5)ccc2c1]

$^1$H NMR (600 MHz, acetonitrile-d$_3$): 2.46-2.57 (m, 4H, H-21a, H-20a, H-13a & H-12a), 2.76-2.84 (m, 2H, H-21b a H-12b), 3.06-3.13 (m, 2H, H-20b & H-13b), 3.98 (s, 3H, H-41), 4.59 (ddd, J=14.6, 12.8, 4.8 Hz, 1H, H-11a), 4.83 (dt, J=13.2, 13.2, 5.7 Hz, 1H, H-22a), 4.98 (dd, J=13.6, 6.1 Hz, 1H, H-22b), 5.50 (dd, J=14.6, 5.9 Hz, 1H, H-11b), 7.27 (d, J=15.8 Hz, 1H, H-30), 7.28 (dd, J=8.9, 2.6 Hz, 1H, H-36), 7.34 (s, 1H, H-3), 7.37 (d, J=2.6 Hz, 1H, H-34), 7.49 (bdd, J=8.4, 1.4 Hz, 1H, H-27), 7.82 (d, J=7.8 Hz, 1H, H-18), 7.83 (d, J=7.8 Hz, 1H, H-19), 7.91 (bd, J=8.6 Hz, 1H, H-33), 7.95 (dd, J=8.6, 1.9 Hz, 1H, H-32), 7.97 (bdq, J=8.9, 3×0.7 Hz, 1H, H-37), 8.02 (bd, J=15.8 Hz, 1H, H-29), 8.03 (ddd, J=7.7, 6.2, 1.4 Hz, 1H, H-25), 8.07 (ddd, J=8.6, 6.9, 0.9 Hz, 1H, H-6), 8.08 (bd, J=1.9 Hz, 1H, H-38), 8.21 (dt, J=7.9, 7.9, 1.5 Hz, 1H, H-26), 8.52 (ddd, J=9.0, 6.9, 1.4 Hz, 1H, H-7), 8.59 (bdq, J=9.0, 3×0.7 Hz, 1H, H-8), 8.80 (dd, J=8.6, 1.4 Hz, 1H, H-5), 9.04 (ddd, J=6.2, 1.5, 0.6 Hz, 1H, H-24).

Example 47

(rac)-13-((1E,3E)-4-(4-methoxy phenyl)buta-1,3-dienyl)-6,7-dimethyl-4,5,8,9-tetrahydroisoquinolino[1,2-a]pyrido[1,2-k][2,9]phenanthroline-3,10-diium trifluoromethanesulfonate

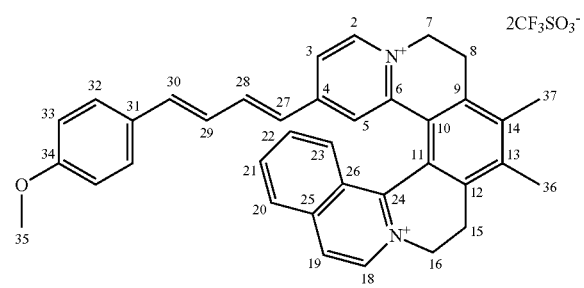 [SMILES: COc1ccc(/C=C/C=C/c2cc[n+]3c(c2)-c2c(c(C)c(C)c4c2-c2c5ccccc5cc[n+]2CC4)CC3)cc1]

$^1$H NMR (600 MHz, acetone-d$_6$): 2.64 (s, 3H, H-36); 2.64 (s, 3H, H-37); 3.40 (bddd, J=5.6, 14.4, 17.0 Hz, 1H, H-8a); 3.48 (bddd, J=4.6, 13.2, 17.0 Hz, 1H, H-15a); 3.80 (ddd, J=1.8, 3.6, 17.0 Hz, 1H, H-15b); 3.82 (ddd, J=1.9, 3.7, 17.0 Hz, 1H, H-8b); 3.88 (s, 3H, H-35); 5.20 (dt, J=3.6, 13.6, 13.6 Hz, 1H, H-16a); 5.22 (dt, 3.7, 14.0, 14.0 Hz, 1H, H-7a); 5.26 (ddd, J=1.9, 5.6, 13.6 Hz, 1H, H-7b); 5.40 (ddd, J=1.8, 4.6, 14.0 Hz, 1H, H-16b); 6.34 (d, J=14.5 Hz, 1H, H-27); 6.83 (ddd, J=0.8, 10.7, 15.4 Hz, 1H, H-29); 6.96 (d, J=15.4 Hz, 1H, H-30); 6.98-7.01 (m, 2H, H-33); 7.12 (ddd, J=0.7, 10.7, 15.4 Hz, 1H, H-28); 7.30 (d, J=2.0 Hz, 1H, H-5); 7.51-7.54 (m, 2H, H-32); 7.79 (dd, J=2.0, 6.6 Hz, 1H, H-3); 7.81 (ddd, J=1.2, 6.9, 8.8 Hz, 1H, H-22); 8.00 (ddd, J=1.0, 6.9, 8.1 Hz, 1H, H-21); 8.15 (dq, J=0.9, 0.9, 0.9, 8.8 Hz, 1H, H-23); 8.27 (ddt, J=0.7, 0.7, 1.2, 8.1 Hz, 1H, H-20); 8.61 (bd, J=6.7 Hz, 1H, H-19); 8.90 (d, J=6.6 Hz, 1H, H-2); 9.12 (d, J=6.7 Hz, 1H, H-18).

Example 48

(rac)-11-((1E,3E)-4-(4-methoxy phenyl)buta-1,3-dienyl)-6,7-dimethyl-4,5,8,9-tetrahydroisoquinolino[1,2-a]pyrido[1,2-k][2,9]phenanthroline-3,10-diium trifluoromethanesulfonate

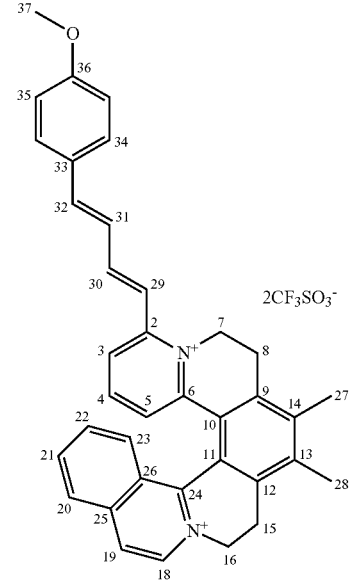 [SMILES: COc1ccc(/C=C/C=C/c2cccc3[n+]2CCc2c(C)c(C)c4c(c2-3)-c2c3ccccc3cc[n+]2CC4)cc1]

$^1$H NMR (600 MHz, acetone-d$_6$): 2.66 (s, 3H, H-27); 2.67 (s, 3H, H-28); 3.35 (bddd, J=4.8, 14.8, 17.4 Hz, 1H, H-8a); 3.49 (ddd, J=4.5, 14.8, 17.2 Hz, 1H, H-15a); 3.82 (ddd, J=1.8, 3.7, 17.2 Hz, 1H, H-15b); 3.86 (ddd, J=2.0, 3.7, 17.4 Hz, 1H, H-8b); 3.86 (s, 3H, H-37); 5.07 (dt, J=3.7, 14.5, 14.5 Hz, 1H, H-7a); 5.18 (bdt, J=3.7, 14.4, 14.4 Hz, 1H, H-16a); 5.40 (ddd, J=1.8, 4.5, 14.0 Hz, 1H, H-16b); 5.60 (ddd, J=2.0, 4.8, 13.7 Hz, 1H, H-7b); 6.81-6.84 (m, 2H, H-35); 7.16 (d, J=15.3 Hz, 1H, H-32); 7.21 (dd, J=10.0, 15.3 Hz, 1H, H-31); 7.30 (dd, J=1.3, 8.0 Hz, 1H, H-5); 7.34 (d, J=14.9 Hz, 1H, H-29); 7.52-7.55 (m, 2H, H-34); 7.66 (t, J=8.1 Hz, 1H, H-4); 7.75 (dd, J=10.0, 14.9 Hz, 1H, H-30); 7.81 (ddd, J=1.2, 6.9, 8.8 Hz, 1H, H-22); 8.01 (ddd, J=1.1, 6.9, 8.1 Hz, 1H, H-21); 8.04 (dd, J=1.3, 8.2 Hz, 1H, H-3); 8.14 (dq, J=0.9, 0.9, 0.9, 8.8 Hz, 1H, H-23); 8.29 (bd, J=8.1 Hz, 1H, H-20); 8.55 (bd, J=6.7 Hz, 1H, H-19); 9.03 (d, J=6.7 Hz, 1H, H-18).

Example 49

2-((1E,3E)-4-(4-methoxy phenyl)buta-1,3-dien-1-yl)-6,7,10,11-tetrahydrodipyrido[2,1-a:1',2'-k][2,9]phenanthroline-5,12-diium trifluoromethanesulfonate

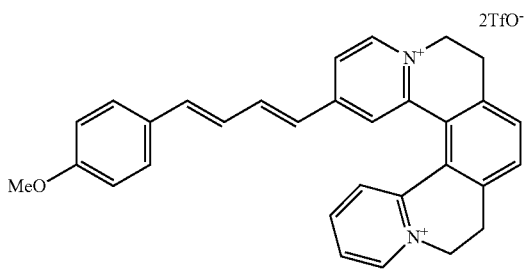 [SMILES: COc1ccc(/C=C/C=C/c2cc[n+]3c(c2)-c2c(ccc4c2-c2cccc[n+]2CC4)CC3)cc1]

$^1$H NMR (400 MHz, acetonitrile-d$_3$): 3.17-3.40 (m, 4H), 3.82 (s, 3H), 4.57-5.00 (m, 4H), 6.52 (d, J=15.4 Hz, 1H), 6.92-6.98 (m, 4H), 7.31 (ddd, J=2.7, 7.2, 15.5 Hz, 1H), 7.49-7.54 (m, 2H), 7.69 (d, J=1.8 Hz, 1H), 7.72 (s, 2H), 7.83 (dd, J=1.9, 6.6 Hz, 1H), 7.89-7.94 (m, 1H), 8.01 (d, J=7.5 Hz, 1H), 8.18 (dt, J=1.4, 8.2 Hz, 1H), 8.54 (d, J=6.7 Hz, 1H), 8.83 (d, J=5.4 Hz, 1H).

Example 50

(rac)-(E)-13-(styryl)-6,7-dimethyl-4,5,8,9-tetrahydroisoquinolino[1,2-a]pyrido[1,2-k][2,9]phenanthroline-3,10-diium trifluoromethanesulfonate

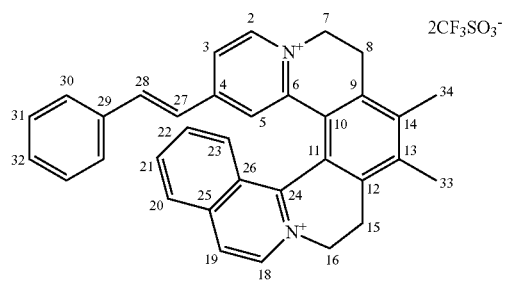

$^1$H NMR (600 MHz, acetoned$_6$): 2.64 (s, 3H, H-33); 2.65 (s, 3H, H-34); 3.40 (ddd, J=5.4, 14.5, 17.0 Hz, 1H, H-8a); 3.47 (bdt, J=4.6, 15.9, 15.9 Hz, 1H, H-15a); 3.81 (ddd, J=1.9, 3.6, 17.0 Hz, 1H, H-8b); 3.82 (ddd, J=1.8, 3.5, 17.0 Hz, 1H, H-15b); 5.24 (dt, J=3.5, 14.5, 14.5, 1H, H-16a); 5.26 (dt, J=3.6, 14.0, 14.0 Hz, 1H, H-7a); 5.31 (ddd, J=1.9, 5.4, 13.6 Hz, 1H, H-7b); 5.39 (ddd, J=1.8, 3.5, 17.0 Hz, 1H, H-16b); 6.97 (d, J=16.3 Hz, 1H, H-27); 7.23 (d, J=16.3 Hz, 1H, H-28); 7.40-7.46 (m, 2H, H-31); 7.40-7.46 (m, 1H, H-32); 7.48 (d, J=2.0 Hz, 1H, H-5); 7.58-7.61 (m, 2H, H-30); 7.80 (ddd, J=1.2, 6.9, 8.7 Hz, 1H, H-22); 7.97 (ddd, J=1.1, 6.9, 8.1 Hz, 1H, H-21); 7.98 (dd, J=2.0, 6.6 Hz, 1H, H-3); 8.14 (dq, J=0.9, 0.9, 0.9, 8.7 Hz, 1H, H-23); 8.22 (bdt, J=0.7, 0.7, 1.2, 8.1 Hz, 1H, H-20); 8.58 (dd, J=0.7, 6.7 Hz, 1H, H-19); 9.00 (d, J=6.6 Hz, 1H, H-2); 9.09 (d, J=6.7 Hz, 1H, H-18).

Example 51

(rac)-(E)-2-styryl-6,7,8,11,12,13-hexahydrodipyrido[1,2-a:1',2'-a']benzo[2,1-c:3,4-c']bisazepinediium trifluoromethanesulfonate

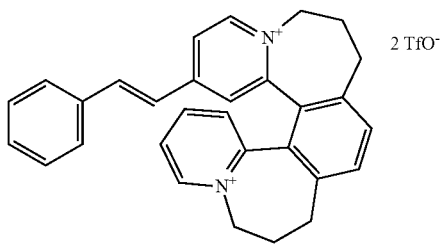 [SMILES: C(=C\c1cc[n+]2c(c1)-c1c(ccc3c1-c1cccc[n+]1CCC3)CCC2)/c1ccccc1]

$^1$H NMR (400 MHz, acetone-d$_6$): 2.43-2.92 (m, 6H), 3.09-3.20 (m, 2H), 4.66-4.84 (m, 1H), 4.83-5.08 (m, 2H), 5.18 (dd, J=13.5, 6.4 Hz, 1H), 7.32 (d, J=16.4 Hz, 1H), 7.39-7.46 (m, 3H), 7.65-7.73 (m, 3H), 7.83 (d, J=16.4 Hz, 1H), 7.86 (s, 2H), 7.92 (dd, J=8.1, 1.4 Hz, 1H), 8.18 (ddd, J=7.7, 6.1, 1.4 Hz, 1H), 8.40 (dd, J=6.7, 2.1 Hz, 1H), 8.45 (td, J=7.9, 1.5 Hz, 1H), 9.16 (d, J=6.7 Hz, 1H), 9.35 (dd, J=6.2, 1.4 Hz, 1H).

Example 52

(rac)-4,15-di((E)-styryl)-6,7,8,11,12,13-hexahydrodipyrido[1,2-a:1',2'-a']benzo[2,1-c:3,4-c']bisazepinediium trifluoromethanesulfonate

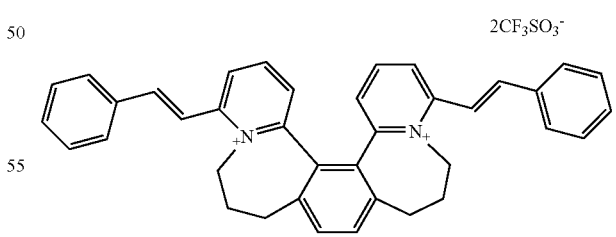

$^1$H NMR (600 MHz, acetonitrile-d$_3$): 2.39 (btt, J=5.6; 5.6; 13.6; 13.6 Hz, 2H), 2.46 (bdt, J=6.8; 13.7; 13.7 Hz, 2H), 2.77 (btt, J=6.0; 6.0; 13.7; 13.7 Hz, 2H), 3.05 (ddd, J=1.0; 6.5; 13.5 Hz, 2H), 4.38 (ddd, J=5.1; 13.5; 14.5 Hz, 2H), 5.06 (dd, J=5.7; 14.5, Hz, 2H), 7.18 (d, J=1.4; 7.8 Hz, 2H), 7.51 (d, J=15.9 Hz, 2H), 7.51-7.56 (m, 4H), 7.51-7.56 (m, 2H), 7.71 (s, 2H), 7.79 (d, J=15.9 Hz, 2H), 7.84-7.86 (m, 4H), 8.11 (ddd, J=0.5; 7.8; 8.3 Hz, 2H), 8.23 (dd, J=1.4; 8.3 Hz, 2H).

Example 53

(rac)-4,15-bis((E)-2-(naphthalene-2-yl)vinyl)-6,7,8,11,12,13-hexahydrodipyrido[1,2-a:1',2'-a']benzo[2,1-c:3,4-c']bisazepinediium trifluoromethanesulfonate

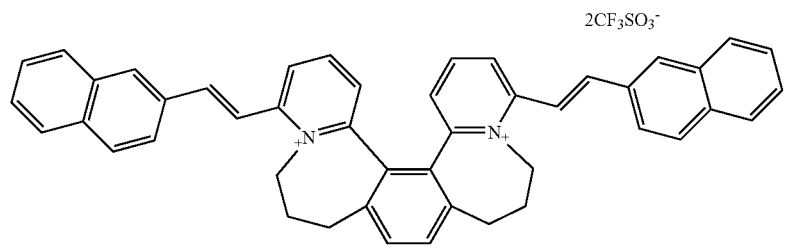 [SMILES: C(=C\c1cccc2[n+]1CCCc1ccc3c(c1-2)-c1cccc(/C=C/c2ccc4ccccc4c2)[n+]1CCC3)/c1ccc2ccccc2c1]

$^1$H NMR (600 MHz, acetonitrile-d$_3$): 2.43 (ddt, J=5.2; 7.0; 13.8; 13.8 Hz, 2H), 2.50 (dt, J=7.0; 13.3; 13.3 Hz, 2H), 2.82 (btt, J=5.9; 5.9; 13.3; 13.3 Hz, 2H), 3.08 (dd, J=5.8; 14.3 Hz, 2H), 4.42 (ddd, J=5.2; 13.5; 14.5 Hz, 2H), 5.12 (dd, J=5.8; 14.5 Hz, 2H), 7.19 (dd, J=1.4; 7.9 Hz, 2H), 7.61-7.65 (m, 2H), 7.61-7.65 (m, 2H), 7.63 (d, J=15.8 Hz, 2H), 7.73 (s, 2H), 7.95 (dd, J=0.6; 15.8 Hz, 2H), 7.97-7.99 (m, 2H), 8.02-8.04 (m, 2H), 8.04 (d, J=8.7 Hz, 2H), 8.05 (dd, J=1.5; 8.7 Hz, 2H), 8.13 (dt, J=0.4; 8.1; 8.1 Hz, 2H), 8.30 (dd, J=1.4; 8.2 Hz, 2H), 8.30 (bdt, J=0.8; 0.8; 1.5 Hz, 2H).

Example 54

(rac)-13-((1E,3E)-4-(phenyl)buta-1,3-dienyl)-6,7-dimethyl-4,5,8,9-tetrahydroisoquinolino[1,2-a]pyrido[1,2-k][2,9]phenanthroline-3,10-diium trifluoromethanesulfonate

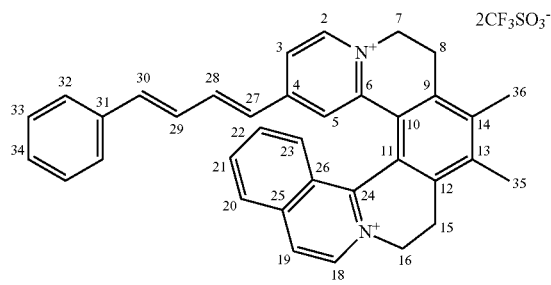 [SMILES: Cc1c(C)c2c(c3c1CC[n+]1ccc(/C=C/C=C/c4ccccc4)cc1-3)-c1c3ccccc3cc[n+]1CC2]

$^1$H NMR (600 MHz, acetone-d$_6$): 2.63 (s, 3H, H-35); 2.64 (s, 3H, H-36); 3.81 (ddd, J=1.9, 3.5, 17.1 Hz, 1H, H-15b); 3.40 (bddd, J=4.6, 15.0, 17.1 Hz, 1H, H-15a); 3.47 (bddd, J=5.3, 14.5, 16.9 Hz, 1H, H-8a); 3.79 (ddd, J=1.9, 3.5, 16.9 Hz, 1H, H-8b); 5.23 (dt, J=3.5, 14.5, 14.5 Hz, 1H, H-16a); 5.23 (dt, J=3.5, 14.0, 14.0 Hz, 1H, H-7a); 5.29 (ddd, J=1.9, 5.3, 13.6 Hz, 1H, H-7b); 5.39 (ddd, J=1.9, 4.6, 14.0 Hz, 1H, H-16b); 6.44 (d, J=15.4 Hz, 1H, H-27); 6.96 (ddd, J=0.7, 9.6, 15.5 Hz, 1H, H-29); 7.00 (d, J=15.5 Hz, 1H, H-30); 7.17 (dd, J=9.6, 15.4 Hz, 1H, H-28); 7.37-7.40 (m, 1H, H-34); 7.39 (d, J=2.0 Hz, 1H, H-5); 7.41-7.44 (m, 2H, H-33); 7.55-7.57 (m, 2H, H-32); 7.80 (ddd, J=1.3, 6.9, 8.7 Hz, 1H, H-22); 7.83 (dd, J=2.0, 6.6 Hz, 1H, H-3); 7.99 (ddd, J=1.1, 6.9, 8.1 Hz, 1H, H-21); 8.15 (dq, J=0.9, 0.9, 0.9, 8.7 Hz, 1H, H-23); 8.26 (ddt, J=0.7, 0.7, 1.3, 8.1 Hz, 1H, H-20); 8.61 (bd, J=6.7 Hz, 1H, H-19); 8.96 (d, J=6.6 Hz, 1H, H-2); 9.12 (d, J=6.7 Hz, 1H, H-18).

II. Biological Tests

Influence of the test compounds on viability (proliferation) of cell lines used was investigated in concentration range 0-100 µmol·l$^{-1}$.

Characterization of Cell Lines Used

Cell lines derived from various cancers are key for complex validation of antiproliferative effects of test compounds in vitro. Testing for evaluation of effects of the studied helquat derivatives was performed with 6 model cancer cell lines and 2 normal (healthy) cell lines of diverse histological origin. All the cell lines listed below were cultivated under conditions for their optimal growth in the given medium in plastic bottles or plastic Petri dishes of various sizes (TPP, BD Biosciences) at 37° C., 5% CO$_2$ and 95% air humidity. HUVEC cells were obtained from BD Biosciences. All other cell lines were obtained from ATCC/LGC Standards (American Type Cell Collection).

CCRF-CEM (Cat. No. ATCC CCL-119)

Suspension cell line CCRF-CEM is a permanent in vitro culture of acute lymphoblastic leukemia. CCRF-CEM cell line was cultivated in RPMI 1640 medium (Sigma-Aldrich, cat. no. R8758) with addition of 2 mmol·l$^{-1}$ glutamine (Invitrogen, cat. no. 35050-038), 10% fetal bovine serum (FBS, Sigma-Aldrich, cat. no. F9665), 100 IU/ml peniciline, 100 µg/ml streptomycine (Sigma-Aldrich, cat. no. P0781). Passaging was performed 2-3× a week. Population doubling time of CCRF-CEM cell line was 20 h under the cultivation conditions used.

HL-60 (Cat. No. ATCC CCL-240)

Suspension cell line HL-60 is a permanent in vitro culture of acute promyelocytic leukemia. HL-60 cell line was cultivated in RPMI 1640 medium (Sigma-Aldrich, see above) with addition of 2 mmol·l$^{-1}$ glutamine (Invitrogen, see above), 10% fetal bovine serum (FBS, Sigma-Aldrich, see above), 100 IU/ml peniciline, 100 µg/ml streptomycine (Sigma-Aldrich, see above). Passaging was performed 2-3× a week. Population doubling time of HL-60 cell line was 23 h under the cultivation conditions used.

MOLT-4 (Cat. No. ATCC CRL-1582)

Suspension cell line MOLT-4 is a permanent in vitro culture of acute lymfoblastic leukemia. Linie MOLT-4 cell line was cultivated in RPMI 1640 medium (Sigma-Aldrich, see above) with addition of 2 mmol glutamine (Invitrogen, see above), 10% fetal bovine serum (FBS, Sigma-Aldrich, see above), 100 IU/ml peniciline, 100 µg/ml streptomycine (Sigma-Aldrich, see above). Passaging was performed 2-3× a week. Population doubling time of MOLT-4 cell line was 25 h under the cultivation conditions used.

HeLa (Cat. No. ATCC CCL-2)

Adherent cell line HeLa is a permanent in vitro culture derived from cervical cancer. HeLa cell line was cultivated in RPMI 1640 medium (Dutch modification) (Sigma-Aldrich, cat. no. R7638) with addition of 2 mmol·l$^{-1}$ glutamine (Invitrogen, see above), 10% fetal bovine serum (FBS, Sigma-Aldrich, see above), 100 IU/ml peniciline, 100 µg/ml streptomycine (Sigma-Aldrich, see above). Passaging was performed twice a week. After washing of cells with sterile PBS the cells were released by 0.25% trypsin/EDTA (Sigma-Aldrich, cat. no. T4049) at 37° C. for 2 minutes. The trypsin was inactivated by addition of 2 volumes of complete medium, cells were then centrifuged (250×g, 5 min), the cell pellet was resuspended, and transferred in the amount needed into a new cultivation bottle with fresh medium. Population doubling time of MOLT-4 cell line was 25 h under the cultivation conditions used.

Hep G2 (Cat. No. ATCC HB-8065)

Adherent cell line Hep G2 is a permanent in vitro culture derived from liver tissue of a patient with hepatocellular carcinoma. Hep G2 cell line was cultivated in DMEM medium (Sigma-Aldrich, cat. no. M4528) with addition of 2 mmol·l$^{-1}$ glutamine (Invitrogen, see above), 10% fetal bovine serum (FBS, Sigma-Aldrich, see above), 100 IU/ml peniciline, 100 µg/ml streptomycine (Sigma-Aldrich, see above). Passaging was performed twice a week. After washing of cells with sterile PBS, the cells were released by 0.25% trypsin/EDTA (Sigma-Aldrich, see above) at 37° C. for 2 minutes. The trypsin was inactivated by addition of 2 volumes of complete medium, cells were then centrifuged (250×g, 5 min), resuspended, and transferred in the amount needed into a new cultivation bottle with fresh medium. Population doubling time of Hep G2 cell line was 28 h under the cultivation conditions used.

LoVo (Cat. No. ATCC CCL-229)

Adherent cell line LoVo is a permanent in vitro culture derived from tissue of a patient with colorectal carcinoma. LoVo cell line was cultivated in DMEM medium (Sigma-Aldrich, cat. no. D8437) with addition of 2 mmol·l$^{-1}$ glutamine (Invitrogen, see above), 10% fetal bovine serum (FBS, Sigma-Aldrich, see above), 100 IU/ml peniciline, 100 µg/ml streptomycine (Sigma-Aldrich, see above). Passaging was performed twice a week. After washing of cells with sterile PBS, the cells were released by 0.25% trypsin/EDTA (Sigma-Aldrich, see above) at 37° C. for 2 minutes. The trypsin was inactivated by addition of 2 volumes of complete medium, cells were then centrifuged (250×g, 5 min), resuspended, and transferred in the amount needed into a new cultivation bottle with fresh medium. Population doubling time of LoVo cell line was 39 h under the cultivation conditions used.

HUVEC (BD Biosciences, Cat. No. 354151)

Normal human endothelial cells from umbilical vein are adherent cells cultivated in plastic Petri dishes coated with collagen I. Into the cultivation medium (E-STIM™; BD Biosciences, cat. co. 355054) already containing 2% FBS (fetal bovine serum), hydrocortisone and heparin the following two further ingredients were added: epidermal growth factor (EGF, 5 µg) and mixture of factors facilitating growth of endothelial cells (ECGS, 100 mg). The cultivation medium used did not contain antibiotics. The cells were passaged after reaching 90% confluency by dissociation using 0.25% solution of trypsin/EDTA (1 ml; 3 min; 37° C.). After that 5 ml of complete cultivation medium E-STIM™ was added and the cells were centrifuged (180×g, 7 min), the pellet was resuspended, and transferred in the amount needed into a new Petri dish with fresh medium. The cells were used in experiments between the 3rd and the 8th passage after defreezing. Population doubling time of HUVEC cell line was 38 h under the cultivation conditions used.

NHDF-Ad (cat. no. ATCC PCS-201-012)

Normal human dermal fibroblasts were cultivated without antibiotics in basal medium for fibroblasts (ATCC/LGC Standards, cat. no. PCS-201-030) with added "Fibroblast Growth Kit-Low serum" (ATCC/LGC Standards, cat. no. PCS-201-041) containing 2% FBS, L-glutamine, hydrocortisone, ascorbic acid, rh FGF beta, rh insulin. When 90% confluency was reached the fibroblasts were washed with sterile PBS (5 ml) and dissociated by addition of 0.25% solution of trypsin/EDTA (2 ml; 2 min; 37° C.). After that 5 ml of cultivation medium for fibroblasts was added and the cells were centrifuged (180×g, 7 min), the cell pellet was resuspended, and transferred in the amount needed into a new cultivation bottle with fresh medium. The same cell release procedure was applied when the cells were to be used in experiments. The cells were used in experiments between the 3rd and the 15th passage after defreeezing. Population doubling time of NHDF-Ad cell line was 33 h under the cultivation conditions used.

Quantitation of Viability of Cancer and Normal Cells after Treatment with Various Concentrations of Test Compounds.

In order to test the sensitivity of the cell lines towards the studied helquats, cytotoxicity test for cell viability assessment based on ATP quantification in cell lysates was used (CellTiter-Glo® Luminescent Cell Viability Assay, Promega, cat. no. G7571). In this test, ATP in cell lysates is detected using luciferase reaction. Luminescence intensity correlates with the ATP level and thus with quantity of metabolically active (viable) cells. $IC_{50}$ value serves as the output, that is the concentration of the test compound which leads to 50% reduction in number of viable cells as compared to control, untreated population. To this end, $IC_{50}$ value reflects efficiency of the test compound with regard to the given cell line.

Cells in the exponential growth phase were seeded into a 96-well microtiter plate were plated at 3000 cells per well. Each well contained 90 µl of cell suspension. The next day, 10 µl of 10× concentrated test compound solutions were added. The effect of helquats was investigated in concentration range 1 to 100 µmol·l$^{-1}$ (e.g. 1; 2.5; 5; 7.5; 10; 15; 25; 50 and 100 µmol·l$^{-1}$). Apart from the section containing the concentration series of the test compound, each well contained 2 control columns, the first with pure medium (so called blank) and the second with cells in medium without the test compounds (control). Into wells containing controls and blanks, volume of solvent (water) equal to the volume of added compound solutions was added. After 72 h of incubation with the test compounds viability was determined according to the manufacturer's instructions. In short: microtiter well plate was left 30 min to reach the room temperature after it has been removed from the incubator. Then, into each well, 100 µl of the prepared detection agent was added. Next, the well plate was shaken for 2 min to complete the full lysis. Next, after the well had been left in the dark for 15 min, the luminescence was measured in each well using luminometer (Tecan Genios, Austria).

TABLE 1

Effect of helquats according to the invention, on cancer cells CCRF-CEM, MOLT-4, HeLa, HL-60, LoVo, Hep G2 and normal (non-cancer) cells HUVEC and NHDF-Ad

| | CCRF-CEM | MOLT-4 | HeLa | HepG2 | HL-60 | LoVo | HUVEC | NHDF-Ad |
|---|---|---|---|---|---|---|---|---|
| (rac)-1 | ** | ** | ** | — | — | — | >150 | * |
| (M)-1 | *** | *** | *** | ** | *** | ** | >150 | * |
| (P)-1 | ** | ** | ** | — | — | — | >150 | * |
| (rac)-7 | *** | ** | ** | — | ** | — | >150 | >150 |
| (M)-7 | *** | *** | *** | ** | *** | ** | * | * |
| (P)-7 | ** | ** | ** | — | ** | — | * | * |
| (rac)-25 | ** | ** | ** | — | ** | * | >150 | >150 |
| 30 | * | * | * | — | — | >150 | >150 | >150 |
| (rac)-35 | * | * | * | — | — | >150 | >150 | >150 |
| (rac)-41 | ** | ** | ** | — | — | ** | * | * |
| (rac)-20 | ** | ** | ** | — | — | * | * | * |
| (M)-6 | ** | ** | ** | ** | ** | ** | >150 | >150 |
| (rac)-12 | ** | * | ** | ** | — | * | * | * |

\*\*\* $IC_{50} = 0\text{-}10\ \mu mol \cdot l^{-1}$
\*\* $IC_{50} = 11\text{-}50\ \mu mol \cdot l^{-1}$
\* $IC_{50} = 51\text{-}150\ \mu mol \cdot l^{-1}$
— $IC_{50}$ value was not determined $IC_{50}$ value represents concentration of the test compound, which leads to 50% reduction of viable cells (inhibition of cell growth) after 72 h of the treatment. Each helquat concentration was tested in triplicates in a $IC_{50}$ quantification and at least 3 independent $IC_{50}$ quantification experiments were performed. $IC_{50}$ values over 100 $\mu mol \cdot l^{-1}$ were obtained by extrapolation of data measured in concentration range 0-100 $\mu mol \cdot l^{-1}$ for the given helquat.

INDUSTRIAL APPLICABILITY

The invention is useful in pharmaceutical industry and medicine for the treatment of diseases related to increased cellular proliferation, for example tumor growth.

The invention claimed is:
1. Helquat derivatives of general formula I

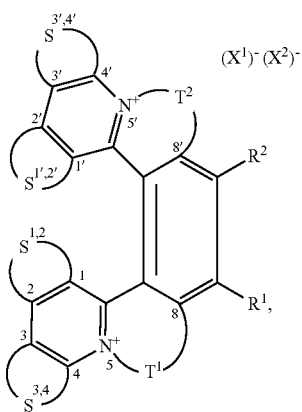

(I)

wherein
substituents $R^1$ and $R^2$ are independently selected from the group comprising H and $C_1$ to $C_3$ alkyl,
up to three of $S^{1,2}$, $S^{1',2'}$, $S^{3,4}$ and $S^{3',4'}$ are present,
$S^{1,2}$, $S^{1',2'}$, $S^{3,4}$ and $S^{3',4'}$ independently represent a linker consisting of a bivalent hydrocarbon chain having 3-6 carbon atoms, and
one or two atoms selected from the carbon atoms with the descriptor 2, 4, 2', and 4' are substituted with a substituent $R^3$ of general formula II

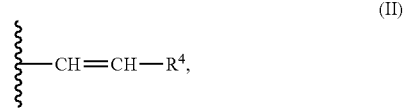

(II)

or general formula III

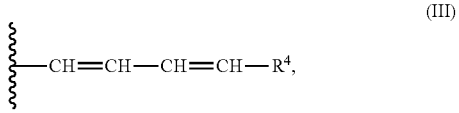

(III)

wherein $R^4$ is substituted or non-substituted aryl,
$T^1$ and $T^2$ independently represent a bivalent hydrocarbon chain having 2-5 carbon atoms,
wherein
aryl is a hydrocarbon group containing 6 to 16 carbon atoms and, and at least one aromatic ring, wherein the aryl can be unsubstituted or substituted with 1 to 5 substituents, selected from a group comprising $C_1$ to $C_6$ alkyl, $C_1$ to $C_6$ halogenoalkyl, $C_1$ to $C_{12}$ alkoxy, aryloxy, benzyloxy, $C_1$ to $C_6$ alkylthio, arylthio, halogeno, —OH, —SH, —NH$_2$, $C_1$ to $C_6$ alkylamino, arylamino, $C_1$ to $C_6$ acylamino, —CN, nitro, and —COOR$_n$,
wherein $R_n$ is hydrogen or $C_1$ to $C_6$ alkyl or aryl;
and anions $(X^1)^-$ and $(X^2)^-$ independently represent anions of pharmaceutically acceptable salts of general formula I.

2. Helquat derivatives according to claim 1 selected from:
(rac)-(E)-13-(4-(dimethylamino)styryl)-6,7-dimethyl-4,5, 8,9-tetrahydroisoquinolino-[1,2-a]pyrido[1,2-k][2,9] phenanthroline-3,10-diium trifluoromethanesulfonate,
(M)-(E)-13-(4-(dimethylamino)styryl)-6,7-dimethyl-4,5, 8,9-tetrahydroisoquinolino-[1,2-a]pyrido[1,2-k][2,9] phenanthroline-3,10-diium trifluoromethanesulfonate, (P)-(E)-13-(4-(dimethylamino)styryl)-6,7-dimethyl-4,5, 8,9-tetrahydroisoquinolino-[1,2-a]pyrido[1,2-k][12,9] phenanthroline-3,10-diium trifluoromethanesulfonate, (rac)-(E)-13-(2-(6-methoxynaphthalene-2-yl)vinyl)-6,7-dimethyl -4,5,8,9-tetrahydroisoquinolino-[1,2-a]pyrido [1,2-k][2,9]phenanthroline-3,10-diium trifluoromethanesulfonate, (M)-(E)-13-(2-(6-methoxynaphthalene-2-yl)vinyl)-6,7-dimethyl-4,5,8,9-tetrahydroisoquinolino-[1,2-a]pyrido [1,2-k][2,9]phenanthroline-3,10-diium trifluoromethanesulfonate, (P)-(E)-13-(2-(6-methoxynaphthalene-2-yl)vinyl)-6,7-dimethyl-4,5,8,9-tetrahydroisoquinolino-[1,2-a]pyrido [1,2-k][2,9]phenanthroline-3,10-diium trifluoromethanesulfonate, (rac)-(E)-11-(2-(1,2,3,5,6,7-hexahydropyrido[3,2,1-ij] quinoline -9-yl)vinyl)-6,7-dimethyl-4,5,8,9-tetrahydroisoquinolino[1,2-a]pyrido[1,2-k][2,9]phenanthroline-3,10-diium trifluoromethanesulfonate, (rac)-(E)-13-(2-(1,2,3,5,6,7-hexahydropyrido[3,2,1-ij] quinoline -9-yl)vinyl)-4,5,8,9-tetrahydro-isoquinolino [2,1-k]pyrido[2,1-a][2,9]phenanthroline-3,10-diium trifluoromethanesulfonate, (rac)-(E)-19-(2-(1,2,3,5,6,7-hexahydropyrido[3,2,1-ij] quinoline -9-yl)vinyl)-8,9,10,13,14,15-hexahydropyrido[1''',2''':1'',2'']azepino[4'',3'':5',6']benzo[1',2':3,4]-azepino[2,1-a]isoquinoline-7,16-diium trifluoromethanesulfonate, 2-((1E,3E)-4-(4-(dimethylamino)phenyl)buta-1,3-dien-1-yl)-6,7,10,11-tetrahydrodipyrido[2,1-a:1',2'-k][2,9] phenanthroline-5,12-diium trifluoromethanesulfonate, (M)-(E)-13-(4-methoxystyryl)-6,7-dimethyl-4,5,8,9-tetrahydroisoquinolino[1,2-a]pyrido-[1,2-k][2,9]phenanthroline-3,10-diium trifluoromethansulfonate, and (rac)-4,15-bis((E)-4-(dimethylamino)styryl)-6,7,8,11,12, 13-hexahydrodipyrido-[1,2-a:1',2'-a']benzo[2,1-c:3,4-c']bisazepinediium trifluoromethanesulfonate.

3. Helquat derivatives of general formula I according to claim 1 for use as medicaments.

4. A medicament comprising at least one helquat derivative of general formula I according to claim 1.

5. Helquat derivatives of general formula I according to claim 1 for use in reducing viability of cancer cells.

6. A method of preparation of helquat derivatives of general formula I as described in claim 1, wherein a starting helquat bearing a reactive methyl group is reacted with substituted or unsubstituted arylaldehyde in the presence of a base, and in an organic solvent, and the resulting product is isolated.

7. The method of preparation according to claim 6, wherein a solvent, selected from methanol, ethanol, acetonitrile, dimethylsulfoxide and dimethylformamide, is used as the organic solvent.

8. A pharmaceutical agent, containing at least one helquat derivative of general formula I according to claim 1 or its pharmaceutically acceptable salt.

9. The pharmaceutical agent according to claim 8, which further contains at least one pharmaceutically acceptable carrier, filler, or diluent.

10. A method of preparation of helquat derivatives of general formula I as described in claim 1, wherein a starting helquat bearing reactive methyl group is reacted with substituted or unsubstituted aryialdebyde in the presence of a base, the base being selected from pyrrolidine and piperidine, and in an organic solvent, and the resulting product is isolated.

* * * * *